United States Patent
Hayter et al.

(10) Patent No.: US 10,136,847 B2
(45) Date of Patent: *Nov. 27, 2018

(54) MITIGATING SINGLE POINT FAILURE OF DEVICES IN AN ANALYTE MONITORING SYSTEM AND METHODS THEREOF

(71) Applicant: Abbott Diabetes Care Inc., Alameda, CA (US)

(72) Inventors: Gary Alan Hayter, Oakland, CA (US); Marc Barry Taub, Mountain View, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/686,153

(22) Filed: Aug. 24, 2017

(65) Prior Publication Data

US 2017/0360336 A1    Dec. 21, 2017

Related U.S. Application Data

(63) Continuation of application No. 15/016,247, filed on Feb. 4, 2016, now Pat. No. 9,743,872, which is a
(Continued)

(51) Int. Cl.
G08B 25/08        (2006.01)
A61B 5/1495       (2006.01)
(Continued)

(52) U.S. Cl.
CPC ........ *A61B 5/1495* (2013.01); *A61B 5/14532* (2013.01); *A61B 5/4839* (2013.01); *A61B 5/742* (2013.01); *A61B 5/7405* (2013.01); *A61B 5/746* (2013.01); *A61B 5/7455* (2013.01); *G08B 21/187* (2013.01); *G08B 23/00* (2013.01);
(Continued)

(58) Field of Classification Search
CPC ... A61B 5/1495; A61B 5/14532; A61B 5/746; A61B 5/7455; A61B 5/7405; A61B 5/742; A61B 5/4839; A61B 2560/0271; A61B 5/0022; A61B 5/002; A61B 2560/0276;
(Continued)

(56) References Cited

U.S. PATENT DOCUMENTS 3,581,062 A    5/1971    Aston
3,926,760 A    12/1975   Allen et al.
(Continued)

FOREIGN PATENT DOCUMENTS

EP    0098592    1/1984
EP    0127958    12/1984
(Continued)

OTHER PUBLICATIONS

Armour, J. C., et al., "Application of Chronic Intravascular Blood Glucose Sensor in Dogs", *Diabetes*, vol. 39, 1990, pp. 1519-1526.
(Continued)

*Primary Examiner* — Anh V La
(74) *Attorney, Agent, or Firm* — Jackson & Co., LLP

(57) ABSTRACT

Methods, devices, and kits are provided for mitigating single point failure of at least one device in an analyte monitoring system.

20 Claims, 6 Drawing Sheets

Related U.S. Application Data continuation of application No. 14/251,542, filed on Apr. 11, 2014, now Pat. No. 9,289,179, which is a continuation of application No. 13/684,078, filed on Nov. 21, 2012, now Pat. No. 8,710,993.

(60) Provisional application No. 61/563,518, filed on Nov. 23, 2011.

(51) Int. Cl.
*A61B 5/145* (2006.01)
*G08B 23/00* (2006.01)
*G08B 21/18* (2006.01)
*A61B 5/00* (2006.01)

(52) U.S. Cl.
CPC .............. *A61B 5/002* (2013.01); *A61B 5/0022* (2013.01); *A61B 2560/0271* (2013.01); *A61B 2560/0276* (2013.01); *A61M 2205/3569* (2013.01)

(58) Field of Classification Search
CPC ................ G08B 23/00; G08B 21/187; A61M 2205/3569
USPC ...... 340/692, 657, 573.1, 521, 501, 3.1, 517, 340/539.1, 539.11, 539.15, 539.21, 522; 600/300, 347
See application file for complete search history.

(56) References Cited

U.S. PATENT DOCUMENTS

| | | |
|---|---|---|
| 3,949,388 A | 4/1976 | Fuller |
| 3,960,497 A | 6/1976 | Acord et al. |
| 4,033,330 A | 7/1977 | Willis et al. |
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,373,527 A | 2/1983 | Fischell |
| 4,392,849 A | 7/1983 | Petre et al. |
| 4,425,920 A | 1/1984 | Bourland et al. |
| 4,431,004 A | 2/1984 | Bessman et al. |
| 4,441,968 A | 4/1984 | Emmer et al. |
| 4,464,170 A | 8/1984 | Clemens et al. |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,619,793 A | 10/1986 | Lee |
| 4,671,288 A | 6/1987 | Gough |
| 4,703,756 A | 11/1987 | Gough et al. |
| 4,731,726 A | 3/1988 | Allen, III |
| 4,749,985 A | 6/1988 | Corsberg |
| 4,757,022 A | 7/1988 | Shults et al. |
| 4,777,953 A | 10/1988 | Ash et al. |
| 4,779,618 A | 10/1988 | Mund et al. |
| 4,847,785 A | 7/1989 | Stephens |
| 4,854,322 A | 8/1989 | Ash et al. |
| 4,871,351 A | 10/1989 | Feingold |
| 4,890,620 A | 1/1990 | Gough |
| 4,925,268 A | 5/1990 | Iyer et al. |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,051,688 A | 9/1991 | Murase et al. |
| 5,055,171 A | 10/1991 | Peck |
| 5,068,536 A | 11/1991 | Rosenthal |
| 5,082,550 A | 1/1992 | Rishpon et al. |
| 5,106,365 A | 4/1992 | Hernandez |
| 5,122,925 A | 6/1992 | Inpyn |
| 5,135,004 A | 8/1992 | Adams et al. |
| 5,165,407 A | 11/1992 | Wilson et al. |
| 5,202,261 A | 4/1993 | Musho et al. |
| 5,204,264 A | 4/1993 | Kaminer et al. |
| 5,210,778 A | 5/1993 | Massart |
| 5,228,449 A | 7/1993 | Christ et al. |
| 5,231,988 A | 8/1993 | Wernicke et al. |
| 5,243,696 A | 9/1993 | Carr et al. |
| 5,246,867 A | 9/1993 | Lakowicz et al. |
| 5,251,126 A | 10/1993 | Kahn et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,320,725 A | 6/1994 | Gregg et al. |
| 5,322,063 A | 6/1994 | Allen et al. |
| 5,330,634 A | 7/1994 | Wong et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,372,427 A | 12/1994 | Padovani et al. |
| 5,379,238 A | 1/1995 | Stark |
| 5,384,547 A | 1/1995 | Lynk et al. |
| 5,390,671 A | 2/1995 | Lord et al. |
| 5,391,250 A | 2/1995 | Cheney, II et al. |
| 5,408,999 A | 4/1995 | Singh et al. |
| 5,410,326 A | 4/1995 | Goldstein |
| 5,411,647 A | 5/1995 | Johnson et al. |
| 5,425,868 A | 6/1995 | Pedersen |
| 5,429,602 A | 7/1995 | Hauser |
| 5,431,160 A | 7/1995 | Wilkins |
| 5,431,921 A | 7/1995 | Thombre |
| 5,438,983 A | 8/1995 | Falcone |
| 5,462,645 A | 10/1995 | Albery et al. |
| 5,472,317 A | 12/1995 | Field et al. |
| 5,489,414 A | 2/1996 | Schreiber et al. |
| 5,497,772 A | 3/1996 | Schulman et al. |
| 5,505,828 A | 4/1996 | Wong et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,532,686 A | 7/1996 | Urbas et al. |
| 5,552,997 A | 9/1996 | Massart |
| 5,555,190 A | 9/1996 | Derby et al. |
| 5,564,434 A | 10/1996 | Halperin et al. |
| 5,568,400 A | 10/1996 | Stark et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,601,435 A | 2/1997 | Quy |
| 5,609,575 A | 3/1997 | Larson et al. |
| 5,628,310 A | 5/1997 | Rao et al. |
| 5,628,324 A | 5/1997 | Sarbach |
| 5,634,468 A | 6/1997 | Platt et al. |
| 5,640,954 A | 6/1997 | Pfeiffer et al. |
| 5,653,239 A | 8/1997 | Pompei et al. |
| 5,660,163 A | 8/1997 | Schulman et al. |
| 5,665,222 A | 9/1997 | Heller et al. |
| 5,707,502 A | 1/1998 | McCaffrey et al. |
| 5,711,001 A | 1/1998 | Bussan et al. |
| 5,711,861 A | 1/1998 | Ward et al. |
| 5,724,030 A | 3/1998 | Urbas et al. |
| 5,726,646 A | 3/1998 | Bane et al. |
| 5,733,259 A | 3/1998 | Valcke et al. |
| 5,735,285 A | 4/1998 | Albert et al. |
| 5,748,103 A | 5/1998 | Flach et al. |

(56) References Cited

U.S. PATENT DOCUMENTS

| | | |
|---|---|---|
| 5,749,907 A | 5/1998 | Mann |
| 5,772,586 A | 6/1998 | Heinonen et al. |
| 5,791,344 A | 8/1998 | Schulman et al. |
| 5,804,047 A | 9/1998 | Karube et al. |
| 5,833,603 A | 11/1998 | Kovacs et al. |
| 5,842,189 A | 11/1998 | Keeler et al. |
| 5,891,049 A | 4/1999 | Cyrus et al. |
| 5,899,855 A | 5/1999 | Brown |
| 5,914,026 A | 6/1999 | Blubaugh, Jr. et al. |
| 5,919,141 A | 7/1999 | Money et al. |
| 5,925,021 A | 7/1999 | Castellano et al. |
| 5,935,224 A | 8/1999 | Svancarek et al. |
| 5,942,979 A | 8/1999 | Luppino |
| 5,951,485 A | 9/1999 | Cyrus et al. |
| 5,957,854 A | 9/1999 | Besson et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,980,708 A | 11/1999 | Champagne et al. |
| 5,995,860 A | 11/1999 | Sun et al. |
| 6,001,067 A | 12/1999 | Shults et al. |
| 6,024,699 A | 2/2000 | Surwit et al. |
| 6,028,413 A | 2/2000 | Brockmann |
| 6,049,727 A | 4/2000 | Crothall |
| 6,052,565 A | 4/2000 | Ishikura et al. |
| 6,066,243 A | 5/2000 | Anderson et al. |
| 6,083,710 A | 7/2000 | Heller et al. |
| 6,088,608 A | 7/2000 | Schulman et al. |
| 6,091,976 A | 7/2000 | Pfeiffer et al. |
| 6,091,987 A | 7/2000 | Thompson |
| 6,093,172 A | 7/2000 | Funderburk et al. |
| 6,096,364 A | 8/2000 | Bok et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,130,623 A | 10/2000 | MacLellan et al. |
| 6,134,461 A | 10/2000 | Say et al. |
| 6,143,164 A | 11/2000 | Heller et al. |
| 6,144,871 A | 11/2000 | Saito et al. |
| 6,157,850 A | 12/2000 | Diab et al. |
| 6,159,147 A | 12/2000 | Lichter et al. |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,223,283 B1 | 4/2001 | Chaiken et al. |
| 6,233,471 B1 | 5/2001 | Berner et al. |
| 6,248,067 B1 | 6/2001 | Causey, III et al. |
| 6,254,586 B1 | 7/2001 | Mann et al. |
| 6,270,455 B1 | 8/2001 | Brown |
| 6,275,717 B1 | 8/2001 | Gross et al. |
| 6,283,761 B1 | 9/2001 | Joao |
| 6,284,478 B1 | 9/2001 | Heller et al. |
| 6,291,200 B1 | 9/2001 | LeJeune et al. |
| 6,293,925 B1 | 9/2001 | Safabash et al. |
| 6,294,997 B1 | 9/2001 | Paratore et al. |
| 6,295,506 B1 | 9/2001 | Heinonen et al. |
| 6,299,347 B1 | 10/2001 | Pompei |
| 6,306,104 B1 | 10/2001 | Cunningham et al. |
| 6,309,884 B1 | 10/2001 | Cooper et al. |
| 6,314,317 B1 | 11/2001 | Willis |
| 6,329,161 B1 | 12/2001 | Heller et al. |
| 6,348,640 B1 | 2/2002 | Navot et al. |
| 6,359,270 B1 | 3/2002 | Bridson |
| 6,359,444 B1 | 3/2002 | Grimes |
| 6,360,888 B1 | 3/2002 | McIvor et al. |
| 6,366,794 B1 | 4/2002 | Moussy et al. |
| 6,377,828 B1 | 4/2002 | Chaiken et al. |
| 6,379,301 B1 | 4/2002 | Worthington et al. |
| 6,387,048 B1 | 5/2002 | Schulman et al. |
| 6,400,974 B1 | 6/2002 | Lesho |
| 6,405,066 B1 | 6/2002 | Essenpreis et al. |
| 6,413,393 B1 | 7/2002 | Van Antwerp et al. |
| 6,416,471 B1 | 7/2002 | Kumar et al. |
| 6,418,346 B1 | 7/2002 | Nelson et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,471,689 B1 | 10/2002 | Joseph et al. |
| 6,478,736 B1 | 11/2002 | Mault |
| 6,484,046 B1 | 11/2002 | Say et al. |
| 6,493,069 B1 | 12/2002 | Nagashimada et al. |
| 6,496,729 B2 | 12/2002 | Thompson |
| 6,497,655 B1 | 12/2002 | Linberg et al. |
| 6,498,043 B1 | 12/2002 | Schulman et al. |
| 6,514,718 B2 | 2/2003 | Heller et al. |
| 6,520,326 B2 | 2/2003 | McIvor et al. |
| 6,544,212 B2 | 4/2003 | Galley et al. |
| 6,546,268 B1 | 4/2003 | Ishikawa et al. |
| 6,549,796 B2 | 4/2003 | Sohrab |
| 6,551,494 B1 | 4/2003 | Heller et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,975 B1 | 5/2003 | Pool et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,545 B2 | 6/2003 | Knobbe et al. |
| 6,574,490 B2 | 6/2003 | Abbink et al. |
| 6,574,510 B2 | 6/2003 | Von Arx et al. |
| 6,576,101 B1 | 6/2003 | Heller et al. |
| 6,577,899 B2 | 6/2003 | Lebel et al. |
| 6,579,231 B1 | 6/2003 | Phipps |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,631,281 B1 | 10/2003 | Kastle |
| 6,633,772 B2 | 10/2003 | Ford et al. |
| 6,635,014 B2 | 10/2003 | Starkweather et al. |
| 6,635,167 B1 | 10/2003 | Batman et al. |
| 6,641,533 B2 | 11/2003 | Causey, III et al. |
| 6,648,821 B2 | 11/2003 | Lebel et al. |
| 6,654,625 B1 | 11/2003 | Say et al. |
| 6,656,114 B1 | 12/2003 | Poulsen et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,675,030 B2 | 1/2004 | Ciuczak et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,721,582 B2 | 4/2004 | Trepagnier et al. |
| 6,730,025 B1 | 5/2004 | Platt |
| 6,731,976 B2 | 5/2004 | Penn et al. |
| 6,733,446 B2 | 5/2004 | Lebel et al. |
| 6,735,183 B2 | 5/2004 | O'Toole et al. |
| 6,740,075 B2 | 5/2004 | Lebel et al. |
| 6,740,518 B1 | 5/2004 | Duong et al. |
| 6,741,877 B1 | 5/2004 | Shults et al. |
| 6,746,582 B2 | 6/2004 | Heller et al. |
| 6,758,810 B2 | 7/2004 | Lebel et al. |
| 6,770,030 B1 | 8/2004 | Schaupp et al. |
| 6,789,195 B1 | 9/2004 | Prihoda et al. |
| 6,790,178 B1 | 9/2004 | Mault et al. |

(56) References Cited

U.S. PATENT DOCUMENTS

| | | |
|---|---|---|
| 6,804,558 B2 | 10/2004 | Haller et al. |
| 6,809,653 B1 | 10/2004 | Maim et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,850,790 B2 | 2/2005 | Berner et al. |
| 6,862,465 B2 | 3/2005 | Shults et al. |
| 6,865,407 B2 | 3/2005 | Kimball et al. |
| 6,873,268 B2 | 3/2005 | Lebel et al. |
| 6,878,112 B2 | 4/2005 | Linberg et al. |
| 6,881,551 B2 | 4/2005 | Heller et al. |
| 6,882,940 B2 | 4/2005 | Potts et al. |
| 6,892,085 B2 | 5/2005 | McIvor et al. |
| 6,895,263 B2 | 5/2005 | Shin et al. |
| 6,895,265 B2 | 5/2005 | Silver |
| 6,923,763 B1 | 8/2005 | Kovatchev et al. |
| 6,923,764 B2 | 8/2005 | Aceti et al. |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,940,403 B2 | 9/2005 | Kail, IV |
| 6,941,163 B2 | 9/2005 | Ford et al. |
| 6,942,518 B2 | 9/2005 | Liamos et al. |
| 6,950,708 B2 | 9/2005 | Bowman, IV et al. |
| 6,954,662 B2 | 10/2005 | Freger et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,983,176 B2 | 1/2006 | Gardner et al. |
| 6,990,366 B2 | 1/2006 | Say et al. |
| 6,997,907 B2 | 2/2006 | Safabash et al. |
| 6,998,247 B2 | 2/2006 | Monfre et al. |
| 6,999,854 B2 | 2/2006 | Roth |
| 7,003,336 B2 | 2/2006 | Holker et al. |
| 7,003,340 B2 | 2/2006 | Say et al. |
| 7,003,341 B2 | 2/2006 | Say et al. |
| 7,009,511 B2 | 3/2006 | Mazar et al. |
| 7,011,630 B2 | 3/2006 | Desai et al. |
| 7,015,817 B2 | 3/2006 | Copley et al. |
| 7,016,713 B2 | 3/2006 | Gardner et al. |
| 7,020,508 B2 | 3/2006 | Stivoric et al. |
| 7,022,072 B2 | 4/2006 | Fox et al. |
| 7,022,219 B2 | 4/2006 | Mansouri et al. |
| 7,024,236 B2 | 4/2006 | Ford et al. |
| 7,024,245 B2 | 4/2006 | Lebel et al. |
| 7,025,425 B2 | 4/2006 | Kovatchev et al. |
| 7,027,848 B2 | 4/2006 | Robinson et al. |
| 7,027,931 B1 | 4/2006 | Jones et al. |
| 7,029,444 B2 | 4/2006 | Shin et al. |
| 7,041,068 B2 | 5/2006 | Freeman et al. |
| 7,041,468 B2 | 5/2006 | Drucker et al. |
| 7,043,305 B2 | 5/2006 | KenKnight et al. |
| 7,046,153 B2 | 5/2006 | Oja et al. |
| 7,052,483 B2 | 5/2006 | Wojcik |
| 7,056,302 B2 | 6/2006 | Douglas |
| 7,058,453 B2 | 6/2006 | Nelson et al. |
| 7,060,031 B2 | 6/2006 | Webb et al. |
| 7,074,307 B2 | 7/2006 | Simpson et al. |
| 7,081,195 B2 | 7/2006 | Simpson et al. |
| 7,082,334 B2 | 7/2006 | Boute et al. |
| 7,092,891 B2 | 8/2006 | Maus et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,123,950 B2 | 10/2006 | Mannheimer |
| 7,125,382 B2 | 10/2006 | Zhou et al. |
| 7,134,999 B2 | 11/2006 | Brauker et al. |
| 7,136,689 B2 | 11/2006 | Shults et al. |
| 7,153,265 B2 | 12/2006 | Vachon |
| 7,155,290 B2 | 12/2006 | Von Arx et al. |
| 7,167,818 B2 | 1/2007 | Brown |
| 7,171,274 B2 | 1/2007 | Starkweather et al. |
| 7,174,199 B2 | 2/2007 | Berner et al. |
| 7,179,226 B2 | 2/2007 | Crothall et al. |
| 7,183,102 B2 | 2/2007 | Monfre et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,203,549 B2 | 4/2007 | Schommer et al. |
| 7,207,974 B2 | 4/2007 | Safabash et al. |
| 7,225,535 B2 | 6/2007 | Feldman et al. |
| 7,226,442 B2 | 6/2007 | Sheppard et al. |
| 7,226,978 B2 | 6/2007 | Tapsak et al. |
| 7,228,182 B2 | 6/2007 | Healy et al. |
| 7,237,712 B2 | 7/2007 | DeRocco et al. |
| 7,258,673 B2 | 8/2007 | Racchini et al. |
| 7,267,665 B2 | 9/2007 | Steil et al. |
| 7,276,029 B2 | 10/2007 | Goode, Jr. et al. |
| 7,278,983 B2 | 10/2007 | Ireland et al. |
| 7,286,894 B1 | 10/2007 | Grant et al. |
| 7,295,867 B2 | 11/2007 | Berner et al. |
| 7,299,082 B2 | 11/2007 | Feldman et al. |
| 7,310,544 B2 | 12/2007 | Brister et al. |
| 7,317,938 B2 | 1/2008 | Lorenz et al. |
| 7,318,816 B2 | 1/2008 | Bobroff et al. |
| 7,324,850 B2 | 1/2008 | Persen et al. |
| 7,335,294 B2 | 2/2008 | Heller et al. |
| 7,347,819 B2 | 3/2008 | Lebel et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,384,397 B2 | 6/2008 | Zhang et al. |
| 7,387,010 B2 | 6/2008 | Sunshine et al. |
| 7,399,277 B2 | 7/2008 | Saidara et al. |
| 7,402,153 B2 | 7/2008 | Steil et al. |
| 7,404,796 B2 | 7/2008 | Ginsberg |
| 7,419,573 B2 | 9/2008 | Gundel |
| 7,424,318 B2 | 9/2008 | Brister et al. |
| 7,460,898 B2 | 12/2008 | Brister et al. |
| 7,467,003 B2 | 12/2008 | Brister et al. |
| 7,468,125 B2 | 12/2008 | Kraft et al. |
| 7,471,972 B2 | 12/2008 | Rhodes et al. |
| 7,474,992 B2 | 1/2009 | Ariyur |
| 7,492,254 B2 | 2/2009 | Bandy et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,519,478 B2 | 4/2009 | Bartkowiak et al. |
| 7,523,004 B2 | 4/2009 | Bartkowiak et al. |
| 7,547,281 B2 | 6/2009 | Hayes et al. |
| 7,565,197 B2 | 7/2009 | Haubrich et al. |
| 7,569,030 B2 | 8/2009 | Lebel et al. |
| 7,574,266 B2 | 8/2009 | Dudding et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,604,178 B2 | 10/2009 | Stewart |
| 7,613,491 B2 | 11/2009 | Boock et al. |
| 7,615,007 B2 | 11/2009 | Shults et al. |
| 7,618,369 B2 | 11/2009 | Hayter et al. |
| 7,630,748 B2 | 12/2009 | Budiman |
| 7,632,228 B2 | 12/2009 | Brauker et al. |
| 7,635,594 B2 | 12/2009 | Holmes et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,651,845 B2 | 1/2010 | Doyle, III et al. |
| 7,653,425 B2 | 1/2010 | Hayter et al. |
| 7,654,956 B2 | 2/2010 | Brister et al. |
| 7,657,297 B2 | 2/2010 | Simpson et al. |
| 7,659,823 B1 | 2/2010 | Killian et al. |
| 7,668,596 B2 | 2/2010 | Von Arx et al. |
| 7,699,775 B2 | 4/2010 | Desai et al. |
| 7,699,964 B2 | 4/2010 | Feldman et al. |
| 7,711,402 B2 | 5/2010 | Shults et al. |
| 7,711,493 B2 | 5/2010 | Bartkowiak et al. |
| 7,713,574 B2 | 5/2010 | Brister et al. |
| 7,715,893 B2 | 5/2010 | Kamath et al. |

(56) References Cited

U.S. PATENT DOCUMENTS

| | | |
|---|---|---|
| 7,736,310 B2 | 6/2010 | Taub et al. |
| 7,741,734 B2 | 6/2010 | Joannopoulos et al. |
| 7,751,864 B2 | 7/2010 | Buck, Jr. |
| 7,766,829 B2 | 8/2010 | Sloan et al. |
| 7,768,386 B2 | 8/2010 | Hayter et al. |
| 7,768,387 B2 | 8/2010 | Fennell et al. |
| 7,771,352 B2 | 8/2010 | Shults et al. |
| 7,774,145 B2 | 8/2010 | Brauker et al. |
| 7,775,444 B2 | 8/2010 | DeRocco et al. |
| 7,778,680 B2 | 8/2010 | Goode et al. |
| 7,779,332 B2 | 8/2010 | Karr et al. |
| 7,782,192 B2 | 8/2010 | Jeckelmann et al. |
| 7,783,333 B2 | 8/2010 | Brister et al. |
| 7,791,467 B2 | 9/2010 | Mazar et al. |
| 7,792,562 B2 | 9/2010 | Shults et al. |
| 7,811,231 B2 | 10/2010 | Jin et al. |
| 7,813,809 B2 | 10/2010 | Strother et al. |
| 7,826,382 B2 | 11/2010 | Sicurello et al. |
| 7,826,981 B2 | 11/2010 | Goode, Jr. et al. |
| 7,831,310 B2 | 11/2010 | Lebel et al. |
| 7,857,760 B2 | 12/2010 | Brister et al. |
| 7,860,574 B2 | 12/2010 | Von Arx et al. |
| 7,882,611 B2 | 2/2011 | Shah et al. |
| 7,885,697 B2 | 2/2011 | Brister et al. |
| 7,889,069 B2 | 2/2011 | Fifolt et al. |
| 7,899,511 B2 | 3/2011 | Shults et al. |
| 7,899,545 B2 | 3/2011 | John |
| 7,905,833 B2 | 3/2011 | Brister et al. |
| 7,912,674 B2 | 3/2011 | Killoren Clark et al. |
| 7,914,450 B2 | 3/2011 | Goode, Jr. et al. |
| 7,916,013 B2 | 3/2011 | Stevenson |
| 7,920,906 B2 | 4/2011 | Goode et al. |
| 7,928,850 B2 | 4/2011 | Hayter et al. |
| 7,938,797 B2 | 5/2011 | Estes |
| 7,941,200 B2 | 5/2011 | Weinert et al. |
| 7,946,984 B2 | 5/2011 | Brister et al. |
| 7,946,985 B2 | 5/2011 | Mastrototaro et al. |
| 7,955,258 B2 | 6/2011 | Goscha et al. |
| 7,970,448 B2 | 6/2011 | Shults et al. |
| 7,972,296 B2 | 7/2011 | Braig et al. |
| 7,974,672 B2 | 7/2011 | Shults et al. |
| 7,976,466 B2 | 7/2011 | Ward et al. |
| 7,978,063 B2 | 7/2011 | Baldus et al. |
| 7,996,158 B2 | 8/2011 | Hayter et al. |
| 7,999,674 B2 | 8/2011 | Kamen |
| 8,005,524 B2 | 8/2011 | Brauker et al. |
| 8,010,174 B2 | 8/2011 | Goode et al. |
| 8,010,256 B2 | 8/2011 | Oowada |
| 8,060,173 B2 | 11/2011 | Goode, Jr. et al. |
| 8,072,310 B1 | 12/2011 | Everhart |
| 8,090,445 B2 | 1/2012 | Ginggen |
| 8,093,991 B2 | 1/2012 | Stevenson et al. |
| 8,094,009 B2 | 1/2012 | Allen et al. |
| 8,098,159 B2 | 1/2012 | Batra et al. |
| 8,098,160 B2 | 1/2012 | Howarth et al. |
| 8,098,161 B2 | 1/2012 | Lavedas |
| 8,098,201 B2 | 1/2012 | Choi et al. |
| 8,098,208 B2 | 1/2012 | Ficker et al. |
| 8,102,021 B2 | 1/2012 | Degani |
| 8,102,154 B2 | 1/2012 | Bishop et al. |
| 8,102,263 B2 | 1/2012 | Yeo et al. |
| 8,102,789 B2 | 1/2012 | Rosar et al. |
| 8,103,241 B2 | 1/2012 | Young et al. |
| 8,103,325 B2 | 1/2012 | Swedlow et al. |
| 8,103,471 B2 | 1/2012 | Hayter |
| 8,111,042 B2 | 2/2012 | Bennett |
| 8,115,488 B2 | 2/2012 | McDowell |
| 8,116,681 B2 | 2/2012 | Baarman |
| 8,116,683 B2 | 2/2012 | Baarman |
| 8,117,481 B2 | 2/2012 | Anselmi et al. |
| 8,120,493 B2 | 2/2012 | Burr |
| 8,124,452 B2 | 2/2012 | Sheats |
| 8,130,093 B2 | 3/2012 | Mazar et al. |
| 8,131,351 B2 | 3/2012 | Kalgren et al. |
| 8,131,365 B2 | 3/2012 | Zhang et al. |
| 8,131,565 B2 | 3/2012 | Dicks et al. |
| 8,132,037 B2 | 3/2012 | Fehr et al. |
| 8,135,352 B2 | 3/2012 | Langsweirdt et al. |
| 8,136,735 B2 | 3/2012 | Arai et al. |
| 8,138,925 B2 | 3/2012 | Downie et al. |
| 8,140,160 B2 | 3/2012 | Pless et al. |
| 8,140,168 B2 | 3/2012 | Olson et al. |
| 8,140,299 B2 | 3/2012 | Siess |
| 8,140,312 B2 | 3/2012 | Hayter et al. |
| 8,150,321 B2 | 4/2012 | Winter et al. |
| 8,150,516 B2 | 4/2012 | Levine et al. |
| 8,160,900 B2 | 4/2012 | Taub et al. |
| 8,170,803 B2 | 5/2012 | Kamath et al. |
| 8,179,266 B2 | 5/2012 | Hermle |
| 8,192,394 B2 | 6/2012 | Estes et al. |
| 8,216,138 B1 | 7/2012 | McGarraugh et al. |
| 8,239,166 B2 | 8/2012 | Hayter et al. |
| 8,255,026 B1 | 8/2012 | Al-Ali |
| 8,260,558 B2 | 9/2012 | Hayter et al. |
| 8,282,549 B2 | 10/2012 | Brauker et al. |
| 8,374,668 B1 | 2/2013 | Hayter et al. |
| 8,376,945 B2 | 2/2013 | Hayter et al. |
| 8,377,271 B2 | 2/2013 | Mao et al. |
| 8,409,093 B2 | 4/2013 | Bugler |
| 8,444,560 B2 | 5/2013 | Hayter et al. |
| 8,461,985 B2 | 6/2013 | Fennell et al. |
| 8,478,557 B2 | 7/2013 | Hayter et al. |
| 8,484,005 B2 | 7/2013 | Hayter et al. |
| 8,543,354 B2 | 9/2013 | Luo et al. |
| 8,560,038 B2 | 10/2013 | Hayter et al. |
| 8,571,808 B2 | 10/2013 | Hayter |
| 8,583,205 B2 | 11/2013 | Budiman et al. |
| 8,597,570 B2 | 12/2013 | Terashima et al. |
| 8,600,681 B2 | 12/2013 | Hayter et al. |
| 8,612,163 B2 | 12/2013 | Hayter et al. |
| 8,657,746 B2 | 2/2014 | Roy |
| 8,682,615 B2 | 3/2014 | Hayter et al. |
| 8,710,993 B2 | 4/2014 | Hayter et al. |
| 8,834,366 B2 | 9/2014 | Hayter et al. |
| 8,845,536 B2 | 9/2014 | Brauker et al. |
| 9,060,719 B2 | 6/2015 | Hayter et al. |
| 9,289,179 B2 | 3/2016 | Hayter et al. |
| 9,398,872 B2 | 7/2016 | Hayter et al. |
| 9,408,566 B2 | 8/2016 | Hayter et al. |
| 9,439,586 B2 | 9/2016 | Bugler |
| 9,483,608 B2 | 11/2016 | Hayter et al. |
| 9,558,325 B2 | 1/2017 | Hayter et al. |
| 9,743,872 B2 * | 8/2017 | Hayter .............. A61B 5/14532 |
| 2001/0037366 A1 | 11/2001 | Webb et al. |
| 2002/0016534 A1 | 2/2002 | Trepagnier et al. |
| 2002/0019022 A1 | 2/2002 | Dunn et al. |
| 2002/0042090 A1 | 4/2002 | Heller et al. |
| 2002/0054320 A1 | 5/2002 | Ogino |
| 2002/0065454 A1 | 5/2002 | Lebel et al. |
| 2002/0068860 A1 | 6/2002 | Clark |
| 2002/0095076 A1 | 7/2002 | Krausman et al. |
| 2002/0103499 A1 | 8/2002 | Perez et al. |
| 2002/0106709 A1 | 8/2002 | Potts et al. |
| 2002/0117639 A1 | 8/2002 | Paolini et al. |
| 2002/0120186 A1 | 8/2002 | Keimel |
| 2002/0128594 A1 | 9/2002 | Das et al. |
| 2002/0147135 A1 | 10/2002 | Schnell |
| 2002/0150959 A1 | 10/2002 | Lejeunne et al. |
| 2002/0161288 A1 | 10/2002 | Shin et al. |
| 2002/0169635 A1 | 11/2002 | Shillingburg |
| 2003/0004403 A1 | 1/2003 | Drinan et al. |
| 2003/0023317 A1 | 1/2003 | Brauker et al. |
| 2003/0023461 A1 | 1/2003 | Quintanilla et al. |
| 2003/0028089 A1 | 2/2003 | Galley et al. |
| 2003/0032077 A1 | 2/2003 | Itoh et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0050546 A1 | 3/2003 | Desai et al. |
| 2003/0054428 A1 | 3/2003 | Monfre et al. |
| 2003/0060692 A1 | 3/2003 | Ruchti et al. |
| 2003/0060753 A1 | 3/2003 | Starkweather et al. |
| 2003/0065308 A1 | 4/2003 | Lebel et al. |
| 2003/0100040 A1 | 5/2003 | Bonnecaze et al. |

(56) References Cited

U.S. PATENT DOCUMENTS

| | | |
|---|---|---|
| 2003/0100821 A1 | 5/2003 | Heller et al. |
| 2003/0114897 A1 | 6/2003 | Von Arx et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0147515 A1 | 8/2003 | Kai et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0191377 A1 | 10/2003 | Robinson et al. |
| 2003/0199744 A1 | 10/2003 | Buse et al. |
| 2003/0199790 A1 | 10/2003 | Boecker et al. |
| 2003/0208113 A1 | 11/2003 | Mault et al. |
| 2003/0212317 A1 | 11/2003 | Kovatchev et al. |
| 2003/0212379 A1 | 11/2003 | Bylund et al. |
| 2003/0216630 A1 | 11/2003 | Jersey-Willuhn et al. |
| 2003/0217966 A1 | 11/2003 | Tapsak et al. |
| 2003/0235817 A1 | 12/2003 | Bartkowiak et al. |
| 2004/0010186 A1 | 1/2004 | Kimball et al. |
| 2004/0010207 A1 | 1/2004 | Flaherty et al. |
| 2004/0011671 A1 | 1/2004 | Shults et al. |
| 2004/0024553 A1 | 2/2004 | Monfre et al. |
| 2004/0034289 A1 | 2/2004 | Teller et al. |
| 2004/0039298 A1 | 2/2004 | Abreu |
| 2004/0040840 A1 | 3/2004 | Mao et al. |
| 2004/0041749 A1 | 3/2004 | Dixon |
| 2004/0045879 A1 | 3/2004 | Shults et al. |
| 2004/0054263 A1 | 3/2004 | Moerman et al. |
| 2004/0063435 A1 | 4/2004 | Sakamoto et al. |
| 2004/0064068 A1 | 4/2004 | DeNuzzio et al. |
| 2004/0099529 A1 | 5/2004 | Mao et al. |
| 2004/0106858 A1 | 6/2004 | Say et al. |
| 2004/0111017 A1 | 6/2004 | Say et al. |
| 2004/0117204 A1 | 6/2004 | Mazar et al. |
| 2004/0122353 A1 | 6/2004 | Shahmirian et al. |
| 2004/0133164 A1 | 7/2004 | Funderburk et al. |
| 2004/0133390 A1 | 7/2004 | Osorio et al. |
| 2004/0135571 A1 | 7/2004 | Uutela et al. |
| 2004/0135684 A1 | 7/2004 | Steinthal et al. |
| 2004/0138588 A1 | 7/2004 | Saikley et al. |
| 2004/0142403 A1 | 7/2004 | Hetzel et al. |
| 2004/0146909 A1 | 7/2004 | Duong et al. |
| 2004/0147872 A1 | 7/2004 | Thompson |
| 2004/0152622 A1 | 8/2004 | Keith et al. |
| 2004/0162678 A1 | 8/2004 | Hetzel et al. |
| 2004/0167464 A1 | 8/2004 | Ireland et al. |
| 2004/0167801 A1 | 8/2004 | Say et al. |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193020 A1 | 9/2004 | Chiba et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199056 A1 | 10/2004 | Husemann et al. |
| 2004/0199059 A1 | 10/2004 | Brauker et al. |
| 2004/0204687 A1 | 10/2004 | Mogensen et al. |
| 2004/0204868 A1 | 10/2004 | Maynard et al. |
| 2004/0219664 A1 | 11/2004 | Heller et al. |
| 2004/0225338 A1 | 11/2004 | Lebel et al. |
| 2004/0236200 A1 | 11/2004 | Say et al. |
| 2004/0249253 A1 | 12/2004 | Racchini et al. |
| 2004/0254433 A1 | 12/2004 | Bandis et al. |
| 2004/0254434 A1 | 12/2004 | Goodnow et al. |
| 2004/0260478 A1 | 12/2004 | Schwamm |
| 2004/0267300 A1 | 12/2004 | Mace |
| 2005/0001024 A1 | 1/2005 | Kusaka et al. |
| 2005/0004439 A1 | 1/2005 | Shin et al. |
| 2005/0004494 A1 | 1/2005 | Perez et al. |
| 2005/0010269 A1 | 1/2005 | Lebel et al. |
| 2005/0017864 A1 | 1/2005 | Tsoukalis |
| 2005/0027177 A1 | 2/2005 | Shin et al. |
| 2005/0027180 A1 | 2/2005 | Goode et al. |
| 2005/0027181 A1 | 2/2005 | Goode et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0038332 A1 | 2/2005 | Saidara et al. |
| 2005/0043598 A1 | 2/2005 | Goode, Jr. et al. |
| 2005/0049179 A1 | 3/2005 | Davidson et al. |
| 2005/0049473 A1 | 3/2005 | Desai et al. |
| 2005/0070774 A1 | 3/2005 | Addison et al. |
| 2005/0070777 A1 | 3/2005 | Cho et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0096516 A1 | 5/2005 | Soykan et al. |
| 2005/0112169 A1 | 5/2005 | Brauker et al. |
| 2005/0113648 A1 | 5/2005 | Yang et al. |
| 2005/0113653 A1 | 5/2005 | Fox et al. |
| 2005/0113886 A1 | 5/2005 | Fischell et al. |
| 2005/0114068 A1 | 5/2005 | Chey et al. |
| 2005/0115832 A1 | 6/2005 | Simpson et al. |
| 2005/0116683 A1 | 6/2005 | Cheng et al. |
| 2005/0121322 A1 | 6/2005 | Say et al. |
| 2005/0131346 A1 | 6/2005 | Douglas |
| 2005/0134731 A1 | 6/2005 | Lee et al. |
| 2005/0137530 A1 | 6/2005 | Campbell et al. |
| 2005/0143635 A1 | 6/2005 | Kamath et al. |
| 2005/0154271 A1 | 7/2005 | Rasdal et al. |
| 2005/0176136 A1 | 8/2005 | Burd et al. |
| 2005/0177398 A1 | 8/2005 | Watanabe et al. |
| 2005/0182306 A1 | 8/2005 | Sloan |
| 2005/0187442 A1 | 8/2005 | Cho et al. |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0196821 A1 | 9/2005 | Monfre et al. |
| 2005/0197793 A1 | 9/2005 | Baker, Jr. |
| 2005/0199494 A1 | 9/2005 | Say et al. |
| 2005/0203360 A1 | 9/2005 | Brauker et al. |
| 2005/0204134 A1 | 9/2005 | Von Arx et al. |
| 2005/0214892 A1 | 9/2005 | Kovatchev et al. |
| 2005/0236361 A1 | 10/2005 | Ufer et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0251033 A1 | 11/2005 | Scarantino et al. |
| 2005/0272985 A1 | 12/2005 | Kotulla et al. |
| 2005/0277164 A1 | 12/2005 | Drucker et al. |
| 2005/0277912 A1 | 12/2005 | John |
| 2005/0287620 A1 | 12/2005 | Heller et al. |
| 2006/0001538 A1 | 1/2006 | Kraft et al. |
| 2006/0001551 A1 | 1/2006 | Kraft et al. |
| 2006/0004270 A1 | 1/2006 | Bedard et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0025663 A1 | 2/2006 | Talbot et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |

(56) References Cited

U.S. PATENT DOCUMENTS

| | | |
|---|---|---|
| 2006/0036145 A1 | 2/2006 | Brister et al. |
| 2006/0058588 A1 | 3/2006 | Zdeblick |
| 2006/0079740 A1 | 4/2006 | Silver et al. |
| 2006/0091006 A1 | 5/2006 | Wang et al. |
| 2006/0142651 A1 | 6/2006 | Brister et al. |
| 2006/0154642 A1 | 7/2006 | Scannell |
| 2006/0155180 A1 | 7/2006 | Brister et al. |
| 2006/0156796 A1 | 7/2006 | Burke et al. |
| 2006/0166629 A1 | 7/2006 | Reggiardo |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0183984 A1 | 8/2006 | Dobbles et al. |
| 2006/0183985 A1 | 8/2006 | Brister et al. |
| 2006/0189851 A1 | 8/2006 | Tvig et al. |
| 2006/0189863 A1 | 8/2006 | Peyser et al. |
| 2006/0193375 A1 | 8/2006 | Lee et al. |
| 2006/0202805 A1 | 9/2006 | Schulman et al. |
| 2006/0211072 A1 | 9/2006 | Ryan et al. |
| 2006/0222566 A1 | 10/2006 | Brauker et al. |
| 2006/0224109 A1 | 10/2006 | Steil et al. |
| 2006/0224141 A1 | 10/2006 | Rush et al. |
| 2006/0229512 A1 | 10/2006 | Petisce et al. |
| 2006/0247508 A1 | 11/2006 | Fennell |
| 2006/0247710 A1 | 11/2006 | Goetz et al. |
| 2006/0247985 A1 | 11/2006 | Liamos et al. |
| 2006/0253296 A1 | 11/2006 | Liisberg et al. |
| 2006/0258929 A1 | 11/2006 | Goode et al. |
| 2006/0272652 A1 | 12/2006 | Stocker et al. |
| 2006/0281985 A1 | 12/2006 | Ward et al. |
| 2006/0287691 A1 | 12/2006 | Drew |
| 2006/0290496 A1 | 12/2006 | Peeters et al. |
| 2006/0293607 A1 | 12/2006 | Alt et al. |
| 2007/0007133 A1 | 1/2007 | Mang et al. |
| 2007/0010950 A1 | 1/2007 | Abensour et al. |
| 2007/0016381 A1 | 1/2007 | Kamath et al. |
| 2007/0017983 A1 | 1/2007 | Frank et al. |
| 2007/0027381 A1 | 2/2007 | Stafford |
| 2007/0027507 A1 | 2/2007 | Burdett et al. |
| 2007/0032706 A1 | 2/2007 | Kamath et al. |
| 2007/0032717 A1 | 2/2007 | Brister et al. |
| 2007/0033074 A1 | 2/2007 | Nitzan et al. |
| 2007/0038044 A1 | 2/2007 | Dobbles et al. |
| 2007/0055799 A1 | 3/2007 | Koehler et al. |
| 2007/0060803 A1 | 3/2007 | Liljetyd et al. |
| 2007/0060814 A1 | 3/2007 | Stafford |
| 2007/0060869 A1 | 3/2007 | Tolle et al. |
| 2007/0060979 A1 | 3/2007 | Strother et al. |
| 2007/0066873 A1 | 3/2007 | Kamath et al. |
| 2007/0066956 A1 | 3/2007 | Finkel |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0078818 A1 | 4/2007 | Zvitz et al. |
| 2007/0093786 A1 | 4/2007 | Goldsmith et al. |
| 2007/0094216 A1 | 4/2007 | Mathias et al. |
| 2007/0100222 A1 | 5/2007 | Mastrototaro et al. |
| 2007/0106135 A1 | 5/2007 | Sloan et al. |
| 2007/0118405 A1 | 5/2007 | Campbell et al. |
| 2007/0124002 A1 | 5/2007 | Estes et al. |
| 2007/0129621 A1 | 6/2007 | Kellogg et al. |
| 2007/0149875 A1 | 6/2007 | Ouyang et al. |
| 2007/0151869 A1 | 7/2007 | Heller et al. |
| 2007/0153705 A1 | 7/2007 | Rosar et al. |
| 2007/0156033 A1 | 7/2007 | Causey, III et al. |
| 2007/0156094 A1 | 7/2007 | Safabash et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0191701 A1 | 8/2007 | Feldman et al. |
| 2007/0191702 A1 | 8/2007 | Yodfat et al. |
| 2007/0202562 A1 | 8/2007 | Curry et al. |
| 2007/0203407 A1 | 8/2007 | Hoss et al. |
| 2007/0203966 A1 | 8/2007 | Brauker et al. |
| 2007/0208244 A1 | 9/2007 | Brauker et al. |
| 2007/0208246 A1 | 9/2007 | Brauker et al. |
| 2007/0213657 A1 | 9/2007 | Jennewine et al. |
| 2007/0228071 A1 | 10/2007 | Kamen et al. |
| 2007/0232878 A1 | 10/2007 | Kovatchev et al. |
| 2007/0232880 A1 | 10/2007 | Siddiqui et al. |
| 2007/0235331 A1 | 10/2007 | Simpson et al. |
| 2007/0244383 A1 | 10/2007 | Talbot et al. |
| 2007/0249922 A1 | 10/2007 | Peyser et al. |
| 2007/0253021 A1 | 11/2007 | Mehta et al. |
| 2007/0255321 A1 | 11/2007 | Gerber et al. |
| 2007/0255348 A1 | 11/2007 | Holtzclaw |
| 2007/0255531 A1 | 11/2007 | Drew |
| 2007/0258395 A1 | 11/2007 | Jollota et al. |
| 2007/0270672 A1 | 11/2007 | Hayter |
| 2007/0271285 A1 | 11/2007 | Eichorn et al. |
| 2007/0282299 A1 | 12/2007 | Hellwig |
| 2007/0285238 A1 | 12/2007 | Batra |
| 2007/0299617 A1 | 12/2007 | Willis |
| 2008/0004515 A1 | 1/2008 | Jennewine et al. |
| 2008/0004601 A1 | 1/2008 | Jennewine et al. |
| 2008/0009692 A1 | 1/2008 | Stafford |
| 2008/0017522 A1 | 1/2008 | Heller et al. |
| 2008/0018433 A1 | 1/2008 | Pitt-Pladdy |
| 2008/0021436 A1 | 1/2008 | Wolpert et al. |
| 2008/0021666 A1 | 1/2008 | Goode, Jr. et al. |
| 2008/0029391 A1 | 2/2008 | Mao et al. |
| 2008/0030369 A1 | 2/2008 | Mann et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0057484 A1 | 3/2008 | Miyata et al. |
| 2008/0058625 A1 | 3/2008 | McGarraugh et al. |
| 2008/0058626 A1 | 3/2008 | Miyata et al. |
| 2008/0058678 A1 | 3/2008 | Miyata et al. |
| 2008/0058773 A1 | 3/2008 | John |
| 2008/0060955 A1 | 3/2008 | Goodnow |
| 2008/0061961 A1 | 3/2008 | John |
| 2008/0064937 A1 | 3/2008 | McGarraugh et al. |
| 2008/0064943 A1 | 3/2008 | Talbot et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071328 A1 | 3/2008 | Haubrich et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0092638 A1 | 4/2008 | Brenneman et al. |
| 2008/0097289 A1 | 4/2008 | Steil et al. |
| 2008/0108942 A1 | 5/2008 | Brister et al. |
| 2008/0114228 A1 | 5/2008 | McCluskey et al. |
| 2008/0119705 A1 | 5/2008 | Patel et al. |
| 2008/0139910 A1 | 6/2008 | Mastrototaro et al. |
| 2008/0154513 A1 | 6/2008 | Kovatchev et al. |
| 2008/0161666 A1 | 7/2008 | Feldman et al. |
| 2008/0167543 A1 | 7/2008 | Say et al. |
| 2008/0167572 A1 | 7/2008 | Stivoric et al. |
| 2008/0172205 A1 | 7/2008 | Breton et al. |
| 2008/0177149 A1 | 7/2008 | Weinert et al. |
| 2008/0177165 A1 | 7/2008 | Blomquist et al. |
| 2008/0182537 A1 | 7/2008 | Manku et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194934 A1 | 8/2008 | Ray et al. |
| 2008/0194935 A1 | 8/2008 | Brister et al. |
| 2008/0194936 A1 | 8/2008 | Goode et al. |

(56) References Cited

U.S. PATENT DOCUMENTS

| | | |
|---|---|---|
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0201325 A1 | 8/2008 | Doniger et al. |
| 2008/0208025 A1 | 8/2008 | Shults et al. |
| 2008/0208026 A1 | 8/2008 | Noujaim et al. |
| 2008/0208113 A1 | 8/2008 | Damian et al. |
| 2008/0214900 A1 | 9/2008 | Fennell et al. |
| 2008/0214910 A1 | 9/2008 | Buck |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0228055 A1 | 9/2008 | Sher |
| 2008/0234663 A1 | 9/2008 | Yodfat et al. |
| 2008/0234943 A1 | 9/2008 | Ray et al. |
| 2008/0235469 A1 | 9/2008 | Drew |
| 2008/0242961 A1 | 10/2008 | Brister et al. |
| 2008/0242963 A1 | 10/2008 | Essenpreis et al. |
| 2008/0254544 A1 | 10/2008 | Modzelewski et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255808 A1 | 10/2008 | Hayter |
| 2008/0256048 A1 | 10/2008 | Hayter |
| 2008/0262469 A1 | 10/2008 | Brister et al. |
| 2008/0269714 A1 | 10/2008 | Mastrototaro et al. |
| 2008/0269723 A1 | 10/2008 | Mastrototaro et al. |
| 2008/0275313 A1 | 11/2008 | Brister et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0294024 A1 | 11/2008 | Cosentino et al. |
| 2008/0296155 A1 | 12/2008 | Shults et al. |
| 2008/0300572 A1 | 12/2008 | Rankers et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312518 A1 | 12/2008 | Jina et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0314395 A1 | 12/2008 | Kovatchev et al. |
| 2008/0319085 A1 | 12/2008 | Wright et al. |
| 2008/0319279 A1 | 12/2008 | Ramsay et al. |
| 2008/0319295 A1 | 12/2008 | Bernstein et al. |
| 2008/0319296 A1 | 12/2008 | Bernstein et al. |
| 2009/0005665 A1 | 1/2009 | Hayter et al. |
| 2009/0005666 A1 | 1/2009 | Shin et al. |
| 2009/0005729 A1 | 1/2009 | Hendrixson et al. |
| 2009/0006034 A1 | 1/2009 | Hayter et al. |
| 2009/0006061 A1 | 1/2009 | Thukral et al. |
| 2009/0006133 A1 | 1/2009 | Weinert et al. |
| 2009/0012376 A1 | 1/2009 | Agus |
| 2009/0012379 A1 | 1/2009 | Goode et al. |
| 2009/0018424 A1 | 1/2009 | Kamath et al. |
| 2009/0018425 A1 | 1/2009 | Ouyang et al. |
| 2009/0030293 A1 | 1/2009 | Cooper et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0040022 A1 | 2/2009 | Finkenzeller |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054745 A1 | 2/2009 | Jennewine et al. |
| 2009/0054747 A1 | 2/2009 | Fennell |
| 2009/0054748 A1 | 2/2009 | Feldman et al. |
| 2009/0054753 A1 | 2/2009 | Robinson et al. |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | Vanantwerp et al. |
| 2009/0063402 A1 | 3/2009 | Hayter |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0085873 A1 | 4/2009 | Betts et al. |
| 2009/0088614 A1 | 4/2009 | Taub et al. |
| 2009/0093687 A1 | 4/2009 | Telfort et al. |
| 2009/0099436 A1 | 4/2009 | Brister et al. |
| 2009/0105554 A1 | 4/2009 | Stahmann et al. |
| 2009/0105560 A1 | 4/2009 | Solomon |
| 2009/0105568 A1 | 4/2009 | Bugler |
| 2009/0105570 A1 | 4/2009 | Sloan et al. |
| 2009/0105571 A1 | 4/2009 | Fennell et al. |
| 2009/0105636 A1 | 4/2009 | Hayter et al. |
| 2009/0112478 A1 | 4/2009 | Mueller, Jr. et al. |
| 2009/0124877 A1 | 5/2009 | Goode et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0149728 A1 | 6/2009 | Van Antwerp et al. |
| 2009/0150186 A1 | 6/2009 | Cohen et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0163855 A1 | 6/2009 | Shin et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0177068 A1 | 7/2009 | Stivoric et al. |
| 2009/0178459 A1 | 7/2009 | Li et al. |
| 2009/0182217 A1 | 7/2009 | Li et al. |
| 2009/0189738 A1 | 7/2009 | Hermle |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0216100 A1 | 8/2009 | Ebner et al. |
| 2009/0216103 A1 | 8/2009 | Brister et al. |
| 2009/0227855 A1 | 9/2009 | Hill et al. |
| 2009/0234200 A1 | 9/2009 | Husheer |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0240440 A1 | 9/2009 | Shurabura et al. |
| 2009/0242399 A1 | 10/2009 | Kamath et al. |
| 2009/0242425 A1 | 10/2009 | Kamath et al. |

(56) References Cited

U.S. PATENT DOCUMENTS

| | | |
|---|---|---|
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0247931 A1 | 10/2009 | Damgaard-Sorensen |
| 2009/0253973 A1 | 10/2009 | Bashan et al. |
| 2009/0259118 A1 | 10/2009 | Feldman et al. |
| 2009/0267765 A1 | 10/2009 | Greene et al. |
| 2009/0287073 A1 | 11/2009 | Boock et al. |
| 2009/0287074 A1 | 11/2009 | Shults et al. |
| 2009/0289796 A1 | 11/2009 | Blumberg |
| 2009/0292188 A1 | 11/2009 | Hoss et al. |
| 2009/0296742 A1 | 12/2009 | Sicurello et al. |
| 2009/0298182 A1 | 12/2009 | Schulat et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010329 A1 | 1/2010 | Taub et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0022988 A1 | 1/2010 | Wochner et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0056992 A1 | 3/2010 | Hayter et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063373 A1 | 3/2010 | Kamath et al. |
| 2010/0064764 A1 | 3/2010 | Hayter et al. |
| 2010/0076283 A1 | 3/2010 | Simpson et al. |
| 2010/0081906 A1 | 4/2010 | Hayter et al. |
| 2010/0081908 A1 | 4/2010 | Dobbles et al. |
| 2010/0081909 A1 | 4/2010 | Budiman et al. |
| 2010/0081910 A1 | 4/2010 | Brister et al. |
| 2010/0081953 A1 | 4/2010 | Syeda-Mahmood et al. |
| 2010/0087724 A1 | 4/2010 | Brauker et al. |
| 2010/0094251 A1 | 4/2010 | Estes et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0105999 A1 | 4/2010 | Dixon et al. |
| 2010/0119693 A1 | 5/2010 | Tapsak et al. |
| 2010/0121167 A1 | 5/2010 | McGarraugh et al. |
| 2010/0121169 A1 | 5/2010 | Petisce et al. |
| 2010/0141656 A1 | 6/2010 | Krieftewirth |
| 2010/0152554 A1 | 6/2010 | Steine et al. |
| 2010/0160759 A1 | 6/2010 | Celentano et al. |
| 2010/0168538 A1 | 7/2010 | Keenan et al. |
| 2010/0168546 A1 | 7/2010 | Kamath et al. |
| 2010/0174266 A1 | 7/2010 | Estes |
| 2010/0185175 A1 | 7/2010 | Kamen et al. |
| 2010/0190435 A1 | 7/2010 | Cook et al. |
| 2010/0191082 A1 | 7/2010 | Brister et al. |
| 2010/0191085 A1 | 7/2010 | Budiman |
| 2010/0191472 A1 | 7/2010 | Doniger et al. |
| 2010/0198034 A1 | 8/2010 | Thomas et al. |
| 2010/0198142 A1 | 8/2010 | Sloan et al. |
| 2010/0204557 A1 | 8/2010 | Kiaie et al. |
| 2010/0213080 A1 | 8/2010 | Celentano et al. |
| 2010/0234710 A1 | 9/2010 | Budiman et al. |
| 2010/0240975 A1 | 9/2010 | Goode et al. |
| 2010/0274111 A1 | 10/2010 | Say et al. |
| 2010/0274515 A1 | 10/2010 | Hoss et al. |
| 2010/0275108 A1 | 10/2010 | Sloan et al. |
| 2010/0292948 A1* | 11/2010 | Feldman ............ A61B 5/14532 702/104 |
| 2010/0312176 A1 | 12/2010 | Lauer et al. |
| 2010/0313105 A1 | 12/2010 | Nekoomaram et al. |
| 2011/0004085 A1 | 1/2011 | Mensinger et al. |
| 2011/0004276 A1 | 1/2011 | Blair et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0031986 A1 | 2/2011 | Bhat et al. |
| 2011/0040163 A1 | 2/2011 | Telson et al. |
| 2011/0054282 A1 | 3/2011 | Nekoomaram et al. |
| 2011/0060530 A1 | 3/2011 | Fennell |
| 2011/0077490 A1 | 3/2011 | Simpson et al. |
| 2011/0077494 A1 | 3/2011 | Doniger et al. |
| 2011/0081726 A1 | 4/2011 | Berman et al. |
| 2011/0112696 A1 | 5/2011 | Yodfat et al. |
| 2011/0148905 A1 | 6/2011 | Simmons et al. |
| 2011/0152637 A1 | 6/2011 | Kateraas et al. |
| 2011/0208027 A1 | 8/2011 | Wagner et al. |
| 2011/0213225 A1 | 9/2011 | Bernstein et al. |
| 2011/0257895 A1 | 10/2011 | Brauker et al. |
| 2011/0282327 A1 | 11/2011 | Kellogg et al. |
| 2011/0287528 A1 | 11/2011 | Fern et al. |
| 2011/0289497 A1 | 11/2011 | Kiaie et al. |
| 2011/0320130 A1 | 12/2011 | Valdes et al. |
| 2011/0320167 A1 | 12/2011 | Budiman |
| 2012/0078071 A1 | 3/2012 | Bohm et al. |
| 2012/0088995 A1 | 4/2012 | Fennell et al. |
| 2012/0108934 A1 | 5/2012 | Valdes et al. |
| 2012/0165626 A1 | 6/2012 | Irina et al. |
| 2012/0165640 A1 | 6/2012 | Galley et al. |
| 2012/0173200 A1 | 7/2012 | Breton et al. |
| 2012/0190989 A1 | 7/2012 | Kaiser et al. |
| 2012/0245447 A1 | 9/2012 | Karan et al. |
| 2013/0035575 A1 | 2/2013 | Mayou et al. |
| 2013/0184547 A1 | 7/2013 | Taub et al. |
| 2013/0225959 A1 | 8/2013 | Bugler |
| 2013/0231541 A1 | 9/2013 | Hayter et al. |
| 2013/0235166 A1 | 9/2013 | Jones et al. |
| 2015/0241407 A1 | 8/2015 | Ou et al. |

FOREIGN PATENT DOCUMENTS

| | | |
|---|---|---|
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| EP | 1568309 | 8/2005 |
| WO | WO-1993/006237 | 4/1993 |
| WO | WO-1996/025089 | 8/1996 |
| WO | WO-1996/035370 | 11/1996 |
| WO | WO-1998/035053 | 8/1998 |
| WO | WO-1999/056613 | 11/1999 |
| WO | WO-2000/049940 | 8/2000 |
| WO | WO-2000/059370 | 10/2000 |
| WO | WO-2000/074753 | 12/2000 |
| WO | WO-2000/078992 | 12/2000 |
| WO | WO-2001/052935 | 7/2001 |
| WO | WO-2001/054753 | 8/2001 |
| WO | WO-2002/016905 | 2/2002 |
| WO | WO-2002/058537 | 8/2002 |
| WO | WO-2003/076893 | 9/2003 |
| WO | WO-2003/082091 | 10/2003 |
| WO | WO-2003/085372 | 10/2003 |
| WO | WO-2004/047445 | 6/2004 |
| WO | WO-2004/061420 | 7/2004 |
| WO | WO-2005/010756 | 2/2005 |

(56) References Cited

FOREIGN PATENT DOCUMENTS

| WO | WO-2005/040404 | 5/2005 |
|---|---|---|
| WO | WO-2005/089103 | 9/2005 |
| WO | WO-2006/024671 | 3/2006 |
| WO | WO-2006/051466 | 5/2006 |
| WO | WO-2006/064397 | 6/2006 |
| WO | WO-2006/079114 | 7/2006 |
| WO | WO-2006/118947 | 11/2006 |
| WO | WO-2007/007459 | 1/2007 |
| WO | WO-2007/097754 | 8/2007 |
| WO | WO-2008/086541 | 7/2008 |
| WO | WO-2010/077329 | 7/2010 |

OTHER PUBLICATIONS

Arnold, M. A., et al., "Selectivity Assessment of Noninvasive Glucose Measurements Based on Analysis of Multivariate Calibration Vectors", *Journal of Diabetes Science and Technology*, vol. 1, No. 4, 2007, pp. 454-462.

Aussedat, B., et al., "A User-Friendly Method for Calibrating a Subcutaneous Glucose Sensor-Based Hypoglycemic Alarm", *Biosensors & Bioelectronics*, vol. 1.2, No. 11, 1997, pp. 1061-1070.

Bennion, N., et al., "Alternate Site Glucose Testing: A Crossover Design", *Diabetes Technology & Therapeutics*, vol. 4, No. 1, 2002, pp. 25-33.

Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.

Boyne, M. S., et al., "Timing of Changes in Interstitial and Venous Blood Glucose Measured With a Continuous Subcutaneous Glucose Sensor", *Diabetes*, vol. 52, Nov. 2003, pp. 2790-2794.

Bremer, T. M., et al., "Benchmark Data from the Literature for Evaluation of New Glucose Sensing Technologies", *Diabetes Technology & Therapeutics*, vol. 3, No. 3, 2001, pp. 409-418.

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Medicated Enzyme Electrode for Amperometric Determination of Glucose", *Analytical Chemistry*, vol. 56, No. 4, 1984, 667-671.

Cheyne, E. H., et al., "Performance of a Continuous Glucose Monitoring System During Controlled Hypoglycaemia in Healthy Volunteers", *Diabetes Technology & Therapeutics*, vol. 4, No. 5, 2002, pp. 607-613.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

El-Khatib, F. H, et al., "Adaptive Closed-Loop Control Provides Blood-Glucose Regulation Using Subcutaneous Insulin and Glucagon Infusion in Diabetic Swine", *Journal of Diabetes Science and Technology*, vol. 1, No. 2, 2007, pp. 181-192.

Eren-Oruklu, M., et al., "Estimation of Future Glucose Concentrations with Subject-Specific Recursive Linear Models", *Diabetes Technology & Therapeutics* vol. 11(4), 2009, pp. 243-253.

Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.

Garg, S., et al., "Improvement in Glycemic Excursions with a Transcutaneous, Real-Time Continuous Glucose Sensor", *Diabetes Care*, vol. 29, No. 1, 2006, pp. 44-50.

Hovorka, R., et al., "Nonlinear Model Predictive Control of Glucose Concentration in Subjects with Type 1 Diabetes", *Physiological Measurement*, vol. 55, Jul. 2004, pp. 905-920.

Isermann, R., "Supervision, Fault-Detection and Fault-Diagnosis Methods—An Introduction", *Control Engineering Practice*, vol. 5, No. 5, 1997, pp. 639-652.

Isermann, R., et al., "Trends in the Application of Model-Based Fault Detection and Diagnosis of Technical Processes", *Control Engineering Practice*, vol. 5, No. 5, 1997, pp. 709-719.

Johnson P. C., "Peripheral Circulation", *John Wiley & Sons*, 1978, pp. 198.

Jungheim, K., et al., "How Rapid Does Glucose Concentration Change in Daily Life of Patients with Type 1 Diabetes?", 2002, pp. 250.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Kovatchev, B. P., et al., "Graphical and Numerical Evaluation of Continuous Glucose Sensing Time Lag", *Diabetes Technology & Therapeutics*, vol. 11, No. 3, 2009, pp. 139-143.

Kuure-Kinsey, M., et al., "A Dual-Rate Kalman Filter for Continuous Glucose Monitoring", *Proceedings of the 28th IEEE, EMBS Annual International Conference*, New York City, 2006, pp. 63-66.

Li, Y., et al., "In Vivo Release From a Drug Delivery MEMS Device", *Journal of Controlled Release*, vol. 100, 2004, pp. 211-219.

Lo, B., et al., "Key Technical Challenges and Current Implementations of Body Sensor Networks", *Body Sensor Networks*, 2005, pp. 1-5.

Lodwig, V., et al., "Continuous Glucose Monitoring with Glucose Sensors: Calibration and Assessment Criteria", *Diabetes Technology & Therapeutics*, vol. 5, No. 4, 2003, pp. 573-587.

Lortz, J., et al., "What is Bluetooth? We Explain the Newest Short-Range Connectivity Technology", *Smart Computing Learning Series, Wireless Computing*, vol. 8, Issue 5, 2002, pp. 72-74.

Malin, S. F., et al., "Noninvasive Prediction of Glucose by Near-Infrared Diffuse Reflectance Spectroscopy", *Clinical Chemistry*, vol. 45, No. 9, 1999, pp. 1651-1658.

McGarraugh, G., et al., "Glucose Measurements Using Blood Extracted from the Forearm and the Finger", *TheraSense, Inc.*, 2001, 16 Pages.

McGarraugh, G., et al., "Physiological Influences on Off-Finger Glucose Testing", *Diabetes Technology & Therapeutics*, vol. 3, No. 3, 2001, pp. 367-376.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

Morbiducci, U, et al., "Improved Usability of the Minimal Model of Insulin Sensitivity Based on an Automated Approach and Genetic Algorithms for Parameter Estimation", *Clinical Science*, vol. 112, 2007, pp. 257-263.

Mougiakakou, et al., "A Real Time Simulation Model of Glucose-Insulin Metabolism for Type 1 Diabetes Patients", *Proceedings of the 2005 IEEE*, 2005, pp. 298-301.

Panteleon, A. E., et al., "The Role of the Independent Variable to Glucose Sensor Calibration", *Diabetes Technology & Therapeutics*, vol. 5, No. 3, 2003, pp. 401-410.

Parker, R., et al., "Robust H∞ Glucose Control in Diabetes Using a Physiological Model", *AIChE Journal*, vol. 46, No. 12, 2000, pp. 2537-2549.

Pickup, J., et al., "Implantable Glucose Sensors: Choosing the Appropriate Sensing Strategy", *Biosensors*, vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Quinn, C. P., et al., "Kinetics of Glucose Delivery to Subcutaneous Tissue in Rats Measured with 0.3-mm Amperometric Microsensors", *The American Physiological Society*, 1995, E155-E161.

(56) References Cited

OTHER PUBLICATIONS

Rodriguez, N., et al., "Flexible Communication and Control Protocol for Injectable Neuromuscular Interfaces", *IEEE Transactions on Biomedical Circuits and Systems*, vol. 1, No. 1, 2007, pp. 19-27.
Roe, J. N., et al., "Bloodless Glucose Measurements", *Critical Review in Therapeutic Drug Carrier Systems*, vol. 15, Issue 3, 1998, pp. 199-241.
Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.
Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.
Salehi, C., et al., "A Telemetry-Instrumentation System for Long-Term Implantable Glucose and Oxygen Sensors", *Analytical Letters*, vol. 29, No. 13, 1996, pp. 2289-2308.
Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.
Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.
Shichiri, M., et al., "Glycaemic Control in Pancreatectomized Dogs with a Wearable Artificial Endocrine Pancreas", *Diabetologia*, vol. 24, 1983, pp. 179-184.
Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.
Shichiri, M., et al., "Membrane Design for Extending the Long-Life of an Implantable Glucose Sensor", *Diabetes Nutrition and Metabolism*, vol. 2, 1989, pp. 309-313.
Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.
Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.
Shichiri, M., et al., "Wearable Artificial Endocrine Pancreas With Needle-Type Glucose Sensor", *The Lancet*, 1982, pp. 1129-1131.
Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.
Steil, G. M., et al., "Closed-Loop Insulin Delivery—the Path of Physiological Glucose Control", *Advanced Drug Delivery Reviews*, vol. 56, 2004, pp. 125-144.
Steil, G. M., et al., "Determination of Plasma Glucose During Rapid Glucose Excursions with a Subcutaneous Glucose Sensor", *Diabetes Technology & Therapeutics*, vol. 5, No. 1, 2003, pp. 27-31.
Sternberg, R., et al., "Study and Development of Multilayer Needle-Type Enzyme-Based Glucose Microsensors", *Biosensors*, vol. 4, 1988, pp. 27-40.
Thompson, M., et al., "In Vivo Probes: Problems and Perspectives", *Clinical Biochemistry*, vol. 19, 1986, pp. 255-261.
Turner, A., et al., "Diabetes Mellitus: Biosensors for Research and Management", *Biosensors*, vol. 1, 1985, pp. 85-115.
Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.
Velho, G., et al., "Strategies for Calibrating a Subcutaneous Glucose Sensor", *Biomedica Biochimica Acta*, vol. 48, 1989, pp. 957-964.
Wilson, G. S., et al., "Progress Toward the Development of an Implantable Sensor for Glucose", *Clinical Chemistry*, vol. 38, No. 9, 1992, pp. 1613-1617.
U.S. Appl. No. 13/684,078, Notice of Allowance dated Feb. 14, 2014.
U.S. Appl. No. 13/684,078, Office Action dated Dec. 27, 2013.
U.S. Appl. No. 14/251,542, Notice of Allowance dated Nov. 25, 2015.
U.S. Appl. No. 14/251,542, Office Action dated Sep. 25, 2015.
U.S. Appl. No. 15/016,247, Office Action dated Dec. 13, 2016.
U.S. Appl. No. 15/016,247, Office Action dated Jun. 17, 2016.
U.S. Appl. No. 15/016,247, Notice of Allowance dated Jun. 15, 2017.

\* cited by examiner

MITIGATING SINGLE POINT FAILURE OF DEVICES IN AN ANALYTE MONITORING SYSTEM AND METHODS THEREOF

RELATED APPLICATIONS

The present application is a continuation of U.S. patent application Ser. No. 15/016,247, now U.S. Pat. No. 9,743,872, which is a continuation of U.S. patent application Ser. No. 14/251,542 filed Apr. 11, 2014, now U.S. Pat. No. 9,289,179, which is a continuation of U.S. patent application Ser. No. 13/684,078 filed Nov. 21, 2012, now U.S. Pat. No. 8,710,993, which claims priority to U.S. Provisional Application No. 61/563,518, filed Nov. 23, 2011, entitled "Mitigating Single Point Failure of Devices in an Analyte Monitoring System and Methods Thereof", the disclosures of each of which are incorporated herein by reference in their entirety for all purposes.

BACKGROUND

The detection of the level of glucose or other analytes, such as lactate, oxygen or the like, in certain individuals is vitally important to their health. For example, the monitoring of glucose is particularly important to individuals with diabetes. Diabetics may need to monitor glucose levels to determine when insulin is needed to reduce glucose levels in their bodies or when additional glucose is needed to raise the level of glucose in their bodies.

Devices have been developed for continuous or automatic monitoring of analytes, such as glucose, in bodily fluid such as in the blood stream or in interstitial fluid. Some of these analyte measuring devices are configured so that at least a portion of the devices are positioned below a skin surface of a user, e.g., in a blood vessel or in the subcutaneous tissue of a user.

SUMMARY

Embodiments of the present disclosure include methods for mitigating single point failure of at least one device in an analyte monitoring system. Certain aspects include requesting that a functionality check of one or more components of a first device be performed and that data related to the functionality check of the one or more components of the first device be communicated to a second device, receiving, information from the first device that is related to functionality of the one or more components of the first device, communicating the information related to the functionality of the one or more components of the first device to a third device, receiving a request from the third device that an alarm be annunciated if it is determined by the third device that the one or more components of the first device is not functioning in accordance with at least one predetermined criterion and annunciating an alarm to alert a user that the one or more components of the first device is not functioning in accordance with the at least one predetermined criterion.

Embodiments of the present disclosure include computer-implemented methods for mitigating single point failure of at least one device in an analyte monitoring. Certain aspects include requesting that a functionality check of one or more components of a first device be performed and that data related to the functionality check of the one or more components of the first device be communicated to a second device, receiving the data related to the functionality of the one or more components of the first device, retrieving a list including at least one predetermined criterion related to the functionality of the one or more components of the first device from a storage component of the second device, comparing the data related to the functionality of the one or more components of the first device with the list including the at least one predetermined criterion and determining if the one or more components of the first device is functioning in accordance with the at least one predetermined criterion.

Embodiments of the present disclosure include computer-implemented methods for mitigating single point failure of at least one device in an analyte monitoring. Certain aspects include requesting that a functionality check of one or more components of a first device be performed and that data related to the functionality check of the one or more components of the first device be communicated to a second device and determining that the one or more components of the first device is not functioning properly if the data related to the functionality check of the components of the first device is not received at the second device, wherein an alarm is annunciated from at least one of the second device or a third device to alert a user that one or more components of the first device is not functioning properly.

DETAILED DESCRIPTION

Before the present disclosure is further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, exemplary methods and materials are now described. All publications mentioned herein are incorporated herein by reference to disclose and describe the methods and/or materials in connection with which the publications are cited.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

Figure 1:
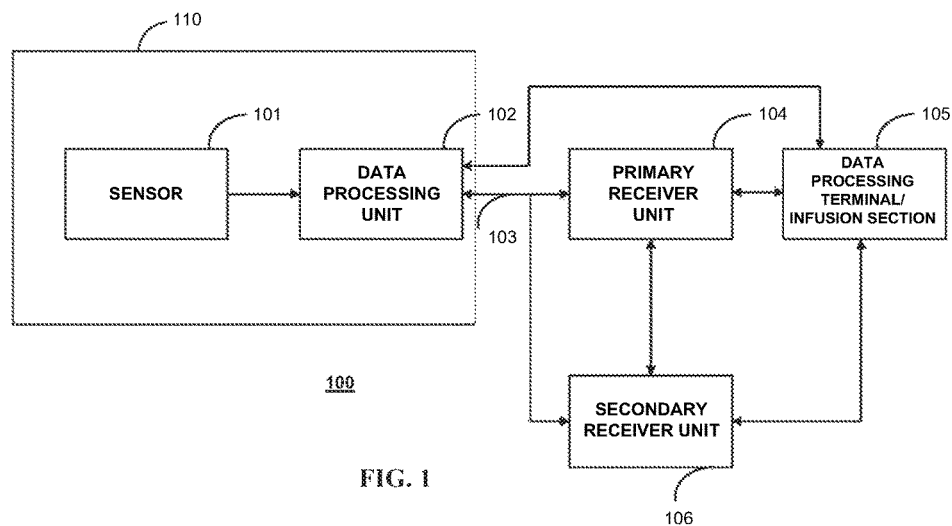
FIG. 1 shows a data monitoring and management system such as, for example, an analyte (e.g., glucose) monitoring system in accordance with certain embodiments of the present disclosure.

FIG. 1 shows a data monitoring and management system such as, for example, an analyte (e.g., glucose) monitoring system in accordance with certain embodiments of the present disclosure. Embodiments of the subject disclosure are described primarily with respect to glucose monitoring devices and systems, and methods of using two or more devices in a glucose monitoring system to reduce the likelihood of a failure of one or more of the devices in the glucose monitoring system going unnoticed by a user.

Analytes that may be monitored include, but are not limited to, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In those embodiments that monitor more than one analyte, the analytes may be monitored at the same or different times.

Referring to FIG. 1, the analyte monitoring system 100 includes a sensor 101, a data processing unit (e.g., sensor electronics) 102 connectable to the sensor 101, and a primary receiver unit 104 which is configured to communicate with the data processing unit 102 via a communication link 103. In aspects of the present disclosure, the sensor 101 and the data processing unit (sensor electronics) 102 may be configured as a single integrated assembly 110. In certain embodiments, the integrated sensor and sensor electronics assembly 110 may be configured as an on-body patch device. In such embodiments, the on-body patch device may be configured for, for example, RFID or RF communication with a reader device/receiver unit, and/or an insulin pump.

In certain embodiments, the primary receiver unit 104 may be further configured to transmit data to a data processing terminal 105 to evaluate or otherwise process or format data received by the primary receiver unit 104. The data processing terminal 105 may be configured to receive data directly from the data processing unit 102 via a communication link which may optionally be configured for bi-directional communication. Further, the data processing unit 102 may include a transmitter or a transceiver to transmit and/or receive data to and/or from the primary receiver unit 104, the data processing terminal 105 or optionally the secondary receiver unit 106.

Also shown in FIG. 1 is an optional secondary receiver unit 106 which is operatively coupled to the communication link and configured to receive data transmitted from the data processing unit 102. The secondary receiver unit 106 may be configured to communicate with the primary receiver unit 104, as well as the data processing terminal 105. The secondary receiver unit 106 may be configured for bi-directional wireless communication with each of the primary receiver unit 104 and the data processing terminal 105. As discussed in further detail below, in certain embodiments the secondary receiver unit 106 may be a de-featured receiver as compared to the primary receiver unit 104, i.e., the secondary receiver unit 106 may include a limited or minimal number of functions and features as compared with the primary receiver unit 104. As such, the secondary receiver unit 106 may include a smaller (in one or more, including all, dimensions), compact housing or embodied in a device such as a wrist watch, arm band, etc., for example. Alternatively, the secondary receiver unit 106 may be configured with the same or substantially similar functions and features as the primary receiver unit 104. The secondary receiver unit 106 may include a docking portion to be mated with a docking cradle unit for placement by, e.g., the bedside for night time monitoring, and/or bi-directional communication device.

Only one sensor 101, data processing unit 102 and data processing terminal 105 are shown in the embodiment of the analyte monitoring system 100 illustrated in FIG. 1. However, it will be appreciated by one of ordinary skill in the art that the analyte monitoring system 100 may include more than one sensor 101 and/or more than one data processing unit 102, and/or more than one data processing terminal 105.

The analyte monitoring system 100 may be a continuous monitoring system, or semi-continuous, or a discrete monitoring system. In a multi-component environment, each component may be configured to be uniquely identified by one or more of the other components in the system so that communication conflict may be readily resolved between the various components within the analyte monitoring system 100. For example, unique IDs, communication channels, and the like, may be used.

In certain embodiments, the sensor 101 is physically positioned in or on the body of a user whose analyte level is being monitored. The sensor 101 may be configured to at least periodically perform a functionality check and convert the results of the functionality check into a corresponding signal for transmission by the data processing unit 102.

The data processing unit 102 is coupleable to the sensor 101 so that both devices are positioned in or on the user's body, with at least a portion of the analyte sensor 101 positioned transcutaneously. The data processing unit 102 in certain embodiments may include a portion of the sensor 101 (proximal section of the sensor in electrical communication with the data processing unit 102) which is encapsulated within or on the printed circuit board of the data processing unit 102 with, for example, potting material or other protective material. The data processing unit 102 performs data processing functions, where such functions may include but are not limited to, filtering and encoding of data signals, each of which corresponds to a sampled analyte level of the user, for transmission to the primary receiver unit 104 via the communication link 103. In one embodiment, the sensor 101 or the data processing unit 102 or a combined sensor/data processing unit may be wholly implantable under the skin layer of the user.

In one aspect, the primary receiver unit 104 may include an analog interface section including an RF receiver and an antenna that is configured to communicate with the data processing unit 102 via the communication link 103, and a data processing section for processing the received data from the data processing unit 102 such as data decoding, error detection and correction, data clock generation, and/or data bit recovery.

In operation, the primary receiver unit 104 in certain embodiments is configured to synchronize with the data processing unit 102 to uniquely identify the data processing unit 102, based on, for example, an identification information of the data processing unit 102, and thereafter, to periodically receive signals transmitted from the data processing unit 102 associated with the monitored analyte levels detected by the sensor 101. That is, when operating in the CGM mode, the receiver unit 104 in certain embodiments is configured to automatically receive data related to the functionality of the sensor from the analyte sensor/sensor electronics when the communication link (e.g., RF range) is maintained between these components.

Referring again to FIG. 1, the data processing terminal 105 may include a personal computer, a portable data processing devices or computers such as a laptop computer or a handheld device (e.g., personal digital assistants (PDAs), communication devices such as a cellular phone (e.g., a multimedia and Internet-enabled mobile phone such as an iPhone, a Blackberry device, a Palm device such as Palm Pre, Treo, or similar phone), mp3 player, pager, and the like), drug delivery device, insulin pump, each of which may be configured for data communication with the receiver via a wired or a wireless connection. Additionally, the data processing terminal 105 may further be connected to a data network (not shown).

The data processing terminal 105 may include an infusion device such as an insulin infusion pump or the like, which may be configured to administer insulin to patients, and which may be configured to communicate with the primary receiver unit 104 for receiving, among others, the measured analyte level. Alternatively, the primary receiver unit 104 may be configured to integrate an infusion device therein so that the primary receiver unit 104 is configured to administer insulin (or other appropriate drug) therapy to patients, for example, for administering and modifying basal profiles, as well as for determining appropriate boluses for administration based on, among others, the detected analyte levels received from the data processing unit 102. An infusion device may be an external device or an internal device (wholly implantable in a user).

In particular embodiments, the data processing terminal 105, which may include an insulin pump, may be configured to receive the functionality signals from the data processing unit 102, and thus, incorporate the functions of the primary receiver unit 104 including data processing for managing the patient's insulin therapy and analyte monitoring. In certain embodiments, the communication link 103 as well as one or more of the other communication interfaces shown in FIG. 1 may use one or more of an RF communication protocol, an infrared communication protocol, a Bluetooth® enabled communication protocol, an 802.11x wireless communication protocol, or an equivalent wireless communication protocol which would allow secure, wireless communication of several units (for example, per HIPAA requirements) while avoiding potential data collision and interference.

As described in aspects of the present disclosure, the analyte monitoring system may include an on-body patch device with a thin profile that can be worn on the arm or other locations on the body (and under clothing worn by the user or the patient), the on-body patch device including an analyte sensor and circuitry and components for operating the sensor and processing and storing signals, including functionality signals, received from the sensor as well as for communication with the reader device. For example, one aspect of the on-body patch device may include electronics to sample the voltage signal received from the analyte sensor in fluid contact with the body fluid, and to process the sampled voltage signals into the corresponding glucose values and/or store the sampled voltage signal as raw data, or to perform a functionality check of its components, and to process the results of the functionality check into a signal or data.

In certain embodiments, the on-body patch device includes an antenna such as a loop antenna to receive RF power from an external device such as the reader device/receiver unit described above, electronics to convert the RF power received via the antenna into DC (direct current) power for the on-body patch device circuitry, communication module or electronics to detect commands received from the reader device, and communication component to transmit data to the reader device, a low capacity battery for providing power to sensor sampling circuitry (for example, the analog front end circuitry of the on-body patch device in signal communication with the analyte sensor), one or more non-volatile memory or storage device to store data including raw signals from the sensor or processed data based on the raw sensor signals. More specifically, in the on operation demand mode, the on-body patch device in certain embodiments is configured to transmit real time analyte related data and/or stored historical analyte related data, and/or functionality data when within the RF power range of the reader device. As such, when the reader device is removed or positioned out of range relative to the on-body patch device, the on-body patch device may no longer transmit the analyte related data and/or functionality data.

In certain embodiments, a data processing module/terminal may be provided in the analyte monitoring system that is configured to operate as a data logger, interacting or communicating with the on-body patch device by, for example, transmitting requests for functionality information to the on-body patch device, and storing the responsive functionality information received from the on-body patch device in one or more memory components of the data processing module (e.g., repeater unit). Further, data processing module may be configured as a compact on-body relay device to relay or retransmit the received analyte level information from the on-body patch device to the reader device/receiver unit or the remote terminal or both. The data processing module in one aspect may be physically coupled to the on-body patch device, for example, on a single adhesive patch on the skin surface of the patient. Alternatively, the data processing module may be positioned close to but not in contact with the on-body patch device. For example, when the on-body patch device is positioned on the abdomen of the patient, the data processing module may be worn on a belt of the patient or the user, such that the desired close proximity or predetermined distance of approximately 1-5 inches (or about 1-10 inches, for example, or more) between the on-body patch device and the data processing module may be maintained.

The various processes described above including the processes operating in the software application execution environment in the analyte monitoring system including the on-body patch device, the reader device, data processing module and/or the remote terminal performing one or more routines described above may be embodied as computer programs developed using an object oriented language that allows the modeling of complex systems with modular objects to create abstractions that are representative of real world, physical objects and their interrelationships. The software required to carry out the inventive process, which may be stored in a memory or storage device of the storage unit of the various components of the analyte monitoring system described above in conjunction to the Figures including the on-body patch device, the reader device, the data processing module, various described communication devices, or the remote terminal may be developed by a person of ordinary skill in the art and may include one or more computer program products.

In one embodiment, an apparatus for bi-directional communication with an analyte monitoring system may comprise a storage device having stored therein one or more routines, a processing unit operatively coupled to the storage device and configured to retrieve the stored one or more routines for execution, a data transmission component operatively coupled to the processing unit and configured to transmit data based at least in part on the one or more routines executed by the processing unit, and a data reception component operatively coupled to the processing unit and configured to receive functionality related data from a remote location and to store the received functionality related data in the storage device for retransmission, wherein the data transmission component is programmed to transmit a query to a remote location, and further wherein the data reception component receives the functionality related data from the remote location in response to the transmitted query when one or more electronics in the remote location transitions from an inactive state to an active state upon detection of the query from the data transmission component.

Figure 2:
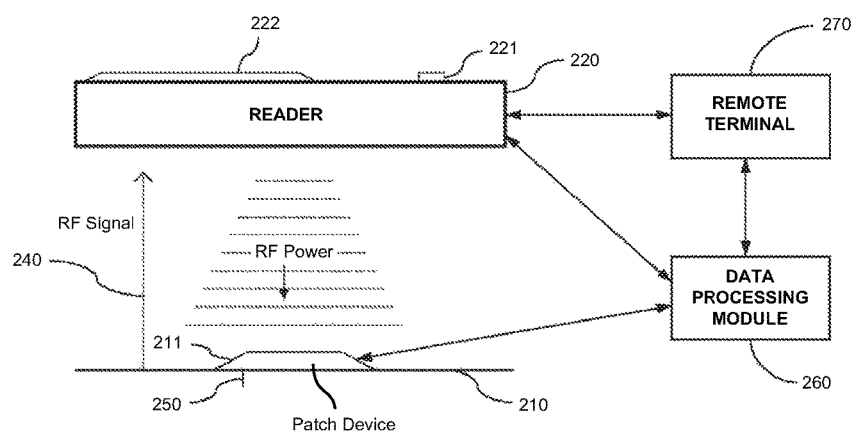
FIG. 2 illustrates a data monitoring and management system for real time glucose measurement data acquisition and processing in one aspect of the present disclosure.

FIG. 2 illustrates a data monitoring and management system for functionality related data acquisition and processing in one aspect of the present disclosure. More specifically, as shown in FIG. 2, the on-body patch device 211 including sensor electronics coupled to an analyte sensor 250 is positioned on a skin surface 210 of a patient or a user.

Referring back to FIG. 2, as shown, when the reader device/receiver unit 220 is positioned or placed in close proximity and within a predetermined range of the on-body patch device 211, the RF power supply in the reader device/receiver unit 220 may be configured to provide the necessary power to operate the electronics in the on-body patch device 211, and the on-body patch device 211 may be configured to, upon detection of the RF power from the reader device/receiver unit 220, perform preprogrammed routines including, for example, transmitting one or more signals 240 to the reader device/receiver unit 220 indicative of the functionality of the components of the analyte sensor 250, or performing functionality check of one or more components of the analyte sensor 250.

In certain embodiments, the reader device/receiver unit 220 may include an RF power switch that is user activatable or activated upon positioning within a predetermined distance from the on-body patch device 211 to turn on the analyte sensor in the on-body patch device 211. That is, using the RF signal, the analyte sensor coupled to the sensor electronics in the on-body patch device 211 may be initialized or activated. In another embodiment, a passive RFID function may be provided or programmed such that upon receiving a "turn on" signal which, when authenticated, will turn on the electronic power switch that activates the on-body patch device 211. That is, the passive RFID configuration may include drawing energy from the RF field radiated from the reader device/receiver unit 220 so as to prompt for and/or detect the "turn on" signal which, upon authentication, activates the on-body patch device 211.

In one embodiment, communication and/or RF power transfer between the reader device/receiver unit 220 and the on-body patch device 211 may be automatically initiated when the reader device/receiver unit 220 is placed in close proximity to the on-body patch device 211 as discussed above. Alternatively, the reader device/receiver unit 220 may be configured such that user activation, such as data request initiation and subsequent confirmation by the user using, for example, the display 222 and/or input components 221 of the reader device/receiver unit 220, may be required prior to the initiation of communication and/or RF power transfer between the reader device/receiver unit 220 and the on-body patch device 211. In a further embodiment, the reader device/receiver unit 220 may be user configurable between multiple modes, such that the user may choose whether the communication between the reader device/receiver unit 220 and on-body patch device 211 is performed automatically or requires a user activation and/or confirmation.

As further shown in FIG. 2, the display 222 of the reader device/receiver unit 220 may be configured to provide the functionalities of a user interface to present information such as alarm or alert notification to the user. In one aspect, the reader device/receiver unit 220 may include other output components such as a speaker, vibratory output component and the like to provide audible and/or vibratory output indication to the user in addition to the visual output indication provided on the display 222.

As discussed, some or all of the electronics in the on-body patch device 211 in one embodiment may be configured to rely on the RF power received from the reader device/receiver unit 220 to perform functionality data processing and/or transmission of the processed functionality information to the reader device/receiver unit 220. That is, the on-body patch device 211 may be discreetly worn on the body of the user or the patient, and under clothing, for example, and when desired, by positioning the reader device/receiver unit 220 within a predetermined distance from the on-body patch device 211, functionality information may be received by the reader device/receiver unit 220.

Referring still to FIG. 2, also shown are a data processing module/terminal 260 and a remote terminal 270. In one aspect, data processing module 260 may include a stand alone device configured for bi-directional communication to communicate with the on-body patch device 211, the reader device/receiver unit 220 and/or the remote terminal 270. More specifically, data processing module 260 may include one or more microprocessors or similar data processing components configured to execute one or more software routines for communication, as well as data storage and retrieval to and from one or more memory components provided in the housing of the data processing module 260.

The data processing module 260 in one embodiment may be configured to communicate with the on-body patch device 211 in a similar manner as the reader device/receiver unit 220 and may include communication components such as antenna, power supply and memory, among others, for example, to allow provision of RF power to the on-body patch device 211 or to request or prompt the on-body patch device 211 to send the functionality related data and optionally stored analyte related data. The data processing module 260 may be configured to interact with the on-body patch device 211 in a similar manner as the reader device/receiver unit 220 such that the data processing module 260 may be positioned within a predetermined distance from the on-body patch device 211 for communication with the on-body patch device 211.

In one aspect, the on-body patch device 211 and the data processing module 260 may be positioned on the skin surface of the user or the patient within the predetermined distance of each other (for example, within approximately 5 inches or less) such that the communication between the on-body patch device 211 and the data processing module 260 is maintained. In a further aspect, the housing of the data processing module 260 may be configured to couple to or cooperate with the housing of the on-body patch device 211 such that the two devices are combined or integrated as a single assembly and positioned on the skin surface.

Referring again to FIG. 2, the data processing module 260 may be configured or programmed to prompt or ping the on-body patch device 211 at a predetermined time interval such as once every minute, or once every five minutes or once every 30 minutes or any other suitable or desired programmable time interval to request functionality related data from the on-body patch device 211 which is received and is stored in one or more memory devices or components of the data processing module 260. In another embodiment, the data processing module 260 is configured to prompt or ping the on-body patch device 211 when desired by the patient or the user on-demand, and not based on a predetermined time interval. In yet another embodiment, the data processing module 260 is configured to prompt or ping the on-body patch device 211 when desired by the patient or the user upon request only after a programmable time interval has elapsed. For example, in certain embodiments, if the user does not initiate communication within a programmed time period, such as, for example 5 hours from last communication (or 10 hours from the last communication), the data processing module 260 may be programmed to automatically ping or prompt the on-body patch device 211 or alternatively, initiate an alarm function to notify the user that an extended period of time has elapsed since the last communication between the data processing module 260 and the on-body patch device 211. In this manner, users, healthcare providers, or the patient may program or configure the data processing module 260 to provide certain compliance with analyte monitoring regimen, to avoid a failure of the analyte sensor device from going unnoticed. Similar functionalities may be provided or programmed in the receiver unit or the reader device in certain embodiments.

As further shown in FIG. 2, the data processing module 260 in one aspect may be configured to transmit the stored data received from the on-body patch device 211 to the reader device/receiver unit 220 when communication between the data processing module 260 and the reader device/receiver unit 220 is established. More specifically, in addition to RF antenna and RF communication components described above, data processing module 260 may include components to communicate using one or more wireless communication protocols such as, for example, but not limited to, infrared (IR) protocol, Bluetooth® protocol, Zigbee® protocol, and 802.11 wireless LAN protocol. Additional description of communication protocols including those based on Bluetooth® protocol and/or Zigbee® protocol can be found in U.S. Patent Publication No. 2006/0193375 incorporated herein by reference for all purposes. The data processing module 260 may further include communication ports, drivers or connectors to establish wired communication with one or more of the reader device/receiver unit 220, on-body patch device 211, or the remote terminal 270 including, for example, but not limited to USB connector and/or USB port, Ethernet connector and/or port, FireWire connector and/or port, or RS-232 port and/or connector.

In one aspect, the data processing module 260 may be configured to operate as a data logger configured or programmed to periodically request or prompt the on-body patch device 211 to transmit the functionality related information, and to store the received information for later retrieval or subsequent transmission to the reader device/receiver unit 220 or to the remote terminal 270 or both, for further processing and analysis.

In a further aspect, the functionalities of the data processing module 260 may be configured or incorporated into a memory device such as an SD card, microSD card, compact flash card, XD card, Memory Stick card, Memory Stick Duo card, or USB memory stick/device including software programming resident in such devices to execute upon connection to the respective one or more of the on-body patch device 211, the remote terminal 270 or the reader device/receiver unit 220. In a further aspect, the functionalities of the data processing module 260, including executable software and programming, may be provided to a communication device such as a mobile telephone including, for example, iPhone, iPod Touch, Blackberry device, Palm based device (such as Palm Pre, Treo, Treo Pro, Centro), personal digital assistants (PDAs) or any other communication enabled operating system (such as Windows or Android operating systems) based mobile telephones as a downloadable application for execution by the downloading communication device. To this end, the remote terminal 270 as shown in FIG. 2 may include a personal computer, or a server terminal that is configured to provide the executable application software to one or more of the communication devices described above when communication between the remote terminal 270 and the devices are established.

Depending upon the user setting or configuration on the communication device, the downloaded application may be programmed or customized using the user interface of the respective communication device (screen, keypad, and the like) to establish or program the desired settings such as a receiver alarm, an insulin pump alarm, sensor replacement alarm, or any other alarm or alert conditions as may be desired by the user. Moreover, the programmed notification settings on the communication device may be output using the output components of the respective communication devices, such as speaker, vibratory output component, or visual output/display. As a further example, the communication device may be provided with programming and application software to communicate with the on-body patch device 211 such that a frequency or periodicity of data acquisition is established. In this manner, the communication device may be configured to conveniently receive functionality information from the on-body patch device 211 at predetermined time periods such as, for example, but not limited to once every minute, once every five minutes, or once every 10 or 15 minutes, and store the received information, as well as to provide a desired or appropriate warning indication or notification to the user or the patient.

Figure 3:
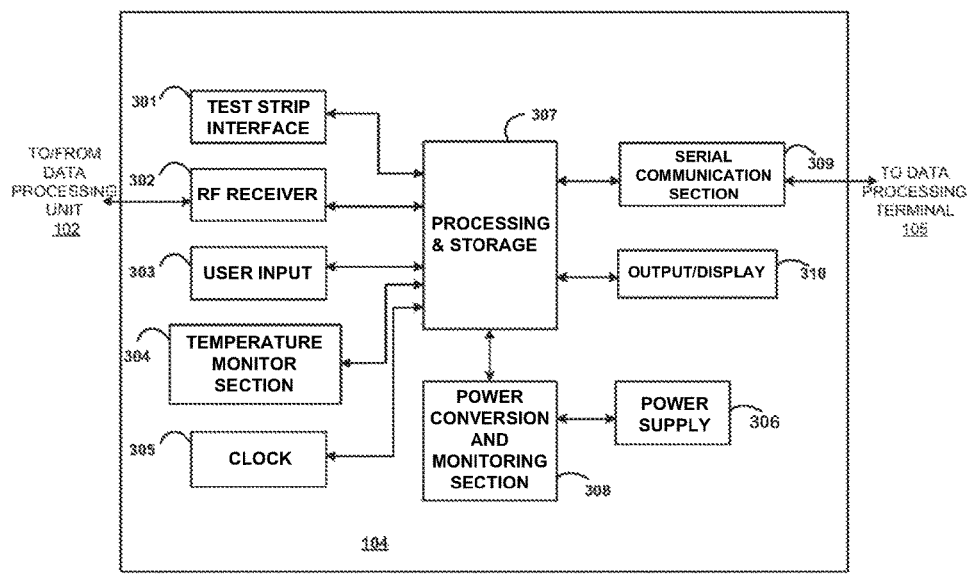
FIG. 3 is a block diagram of a receiver/monitor unit such as that shown in FIG. 1 in accordance with certain embodiments.

FIG. 3 is a block diagram of a receiver/monitor unit or insulin pump such as that shown in FIG. 1 in accordance with certain embodiments. The primary receiver unit 104 (FIG. 1) includes one or more of: a blood glucose test strip interface 301, an RF receiver 302, an input 303, a temperature detection section 304, and a clock 305, each of which is operatively coupled to a processing and storage section 307. The primary receiver unit 104 also includes a power supply 306 operatively coupled to a power conversion and monitoring section 308. Further, the power conversion and monitoring section 308 is also coupled to the receiver processor 307. Moreover, also shown are a receiver serial communication section 309, and an output 310, each operatively coupled to the processing and storage unit 307. The receiver may include user input and/or interface components or may be free of user input and/or interface components.

In one aspect, the RF receiver 302 is configured to communicate, via the communication link 103 (FIG. 1) with the data processing unit (sensor electronics) 102, to receive encoded data from the data processing unit 102 for, among others, signal mixing, demodulation, and other data processing. The input 303 of the primary receiver unit 104 is configured to allow the user to enter information into the primary receiver unit 104 as needed. In one aspect, the input 303 may include keys of a keypad, a touch-sensitive screen, and/or a voice-activated input command unit, and the like. The temperature monitor section 304 may be configured to provide temperature information of the primary receiver unit 104 to the processing and control section 307, while the clock 305 provides, among others, real time or clock information to the processing and storage section 307.

Each of the various components of the primary receiver unit 104 shown in FIG. 3 is powered by the power supply 306 (or other power supply) which, in certain embodiments, includes a battery. Furthermore, the power conversion and monitoring section 308 is configured to monitor the power usage by the various components in the primary receiver unit 104 for effective power management and may alert the user, for example, in the event of power usage which renders the primary receiver unit 104 in sub-optimal operating conditions. The serial communication section 309 in the primary receiver unit 104 is configured to provide a bi-directional communication path from the testing and/or manufacturing equipment for, among others, initialization, testing, and configuration of the primary receiver unit 104.

Serial communication section 309 can also be used to upload data to a computer, such as functionality related data. The communication link with an external device (not shown) can be made, for example, by cable (such as USB or serial cable), infrared (IR) or RF link. The output/display 310 of the primary receiver unit 104 is configured to provide, among others, a graphical user interface (GUI), and may include a liquid crystal display (LCD) for displaying information. Additionally, the output/display 310 may also include an integrated speaker for outputting audible signals as well as to provide vibration output as commonly found in handheld electronic devices, such as mobile telephones, pagers, etc. In certain embodiments, the primary receiver unit 104 also includes an electro-luminescent lamp configured to provide backlighting to the output 310 for output visual display in dark ambient surroundings.

Referring back to FIG. 3, the primary receiver unit 104 may also include a storage section such as a programmable, non-volatile memory device as part of the processor 307, or provided separately in the primary receiver unit 104, operatively coupled to the processor 307. The processor 307 may be configured to perform Manchester decoding (or other protocol(s)) as well as error detection and correction upon the encoded data received from the data processing unit 102 via the communication link 103.

In further embodiments, the data processing unit 102 and/or the primary receiver unit 104 and/or the secondary receiver unit 106, and/or the data processing terminal/infusion section 105 of FIG. 1 may be configured to receive the blood glucose value wirelessly over a communication link from, for example, a blood glucose meter. In further embodiments, a user manipulating or using the analyte monitoring system 100 (FIG. 1) may manually input the blood glucose value using, for example, a user interface (for example, a keyboard, keypad, voice commands, and the like) incorporated in the one or more of the data processing unit 102, the primary receiver unit 104, secondary receiver unit 106, or the data processing terminal/infusion section 105.

Additional detailed descriptions are provided in U.S. Pat. Nos. 5,262,035; 5,264,104; 5,262,305; 5,320,715; 5,593,852; 6,175,752; 6,650,471; 6,746,582; 6,284,478; 7,299,082; and 7,811,231; in U.S. application Ser. No. 11/060,365 filed Feb. 16, 2005 titled "Method and System for Providing Data Communication in Continuous Glucose Monitoring And Management System", now U.S. Pat. No. 8,771,183, in U.S. application Ser. No. 12/698,124 filed Feb. 1, 2010 titled "Compact On-Body Physiological Monitoring Devices and Methods Thereof", and in U.S. application Ser. No. 12/807,278 filed Aug. 31, 2010 titled "Medical Devices and Methods", each of which is incorporated herein by reference.

A safety issue with the receiver device, continuous glucose monitors (CGMs), repeater unit, and insulin pumps in an analyte monitoring system is the susceptibility to single point failure associated with each device's microprocessor, power supply, audio annunciators, transmitter, and transceiver. Introducing a power supply monitoring circuit, a microprocessor monitoring circuit, a secondary power supply, and/or audio annunciator (or vibrator) to the device will provide redundancy that will reduce the likelihood of a failure going unnoticed by the user; however, including these components is costly in terms of expense and product size. The embodiments of the present disclosure provide additional protection against single point failures in systems made up of two or more devices. Essentially, each device in the analyte monitoring system is monitored by one or more of the other devices in the system.

In certain integrated CGM and insulin pump system embodiments, where both devices contain at least one microprocessor, power supply, and audio annunciator or other alarm mechanism, in one embodiment, each device can perform a periodic self test and report this to the other device. Each device has a monitoring process that would initiate an alarm if the other device does not report a successful self test. In some embodiments, the monitoring device could poll the other device, and even initiate the self test on the other device. Also, different functionality could be tested and/or reported on different test schedules.

The applicability of this functionality depends on how necessary periodic communication between the devices is to the function of the system. For instance, in certain embodiments where the receiver device of a continuous analyte monitoring system may not need to be in communication, such as RF communication, range with an insulin pump for the insulin pump to function, this feature could be optional, e.g., configured by the user, a parent of the user, and/or a physician. In other embodiments, such as for a closed loop control system where the control algorithm is maintained in the receiver device, frequent communication is needed between the handheld and the pump, and therefore continuous knowledge of the functionality of both devices is vital.

Figure 4:
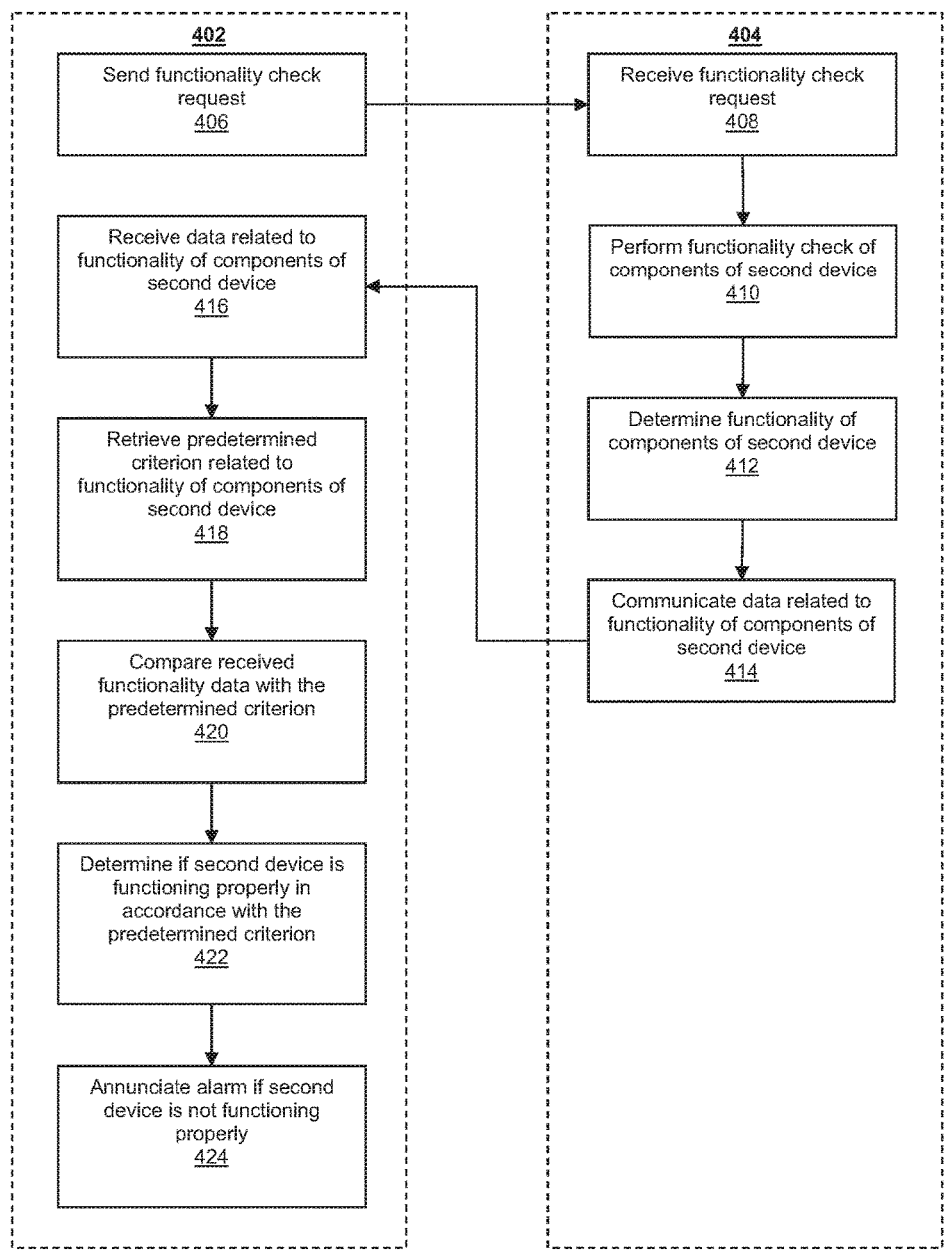
FIG. 4 is a flowchart illustrating a method for mitigating single point failure of at least one device in an analyte monitoring system in accordance with certain embodiments of the present disclosure.

FIG. 4 is a flow diagram illustrating steps in an embodiment for mitigating single point failure of at least one device in an analyte monitoring system 400. The first device 402 and the second device 404 in the analyte monitoring system 400 can be at least one of a receiver device, an analyte meter, a glucose monitor, an insulin pump, a continuous analyte monitor, a cellular phone, a personal digital assistant, a personal computer, a laptop computer, and/or a repeater unit. In certain embodiments, a first device 402 sends a request that a functionality check of the components of a second device 404 be performed (406). The request can be sent, for example, wirelessly from the transmitter of the first device 402 to the transceiver of the second device 404. The components of the second device 404 can include at least one of a microprocessor, a power supply, a sensor, an electronic component, and a storage device.

The second device 404 receives the request to perform a functionality check of the second device 404 from the first device 402 (408) and performs the functionality check of its components (410). In certain embodiments, the second device 404 only performs the functionality check if the second device 404 has the capacity to perform the check. A functionality check, or "self-test", is a standard feature of most electronic devices. The functionality check of the components can include a determination of the current, voltage, and/or resistance that can be measured across an electrical circuit in the one or more components. The functionality check can include component testing that applies an input to the various components being tested, and receives an output based on the input. The functionality check may also include checking digital system components, such as a checksum for a block of memory. Any of a number of common techniques used in electronic devices can be applied to the functionality check of the present disclosure. In addition, some components of the devices in the analyte monitoring system may have built in self-test functionality that can be queried. For instance, a power supply module may have a digital self-test status output that can be queried by the processor in order to determine the functionality of the power supply. A device may have electronic circuitry that includes electronic or mechanical switches that allow testing of the electronic circuitry. The switch, for example, could route the current path for functional test across the speaker circuit to test for the proper speaker resistance, in order to detect any open or short circuits.

Referring still to FIG. 4, the second device 404 determines the functionality of its components based on the outcome of the functionality check (412) and the second device 404 communicates data related to the determined functionality of its components to the first device 402 (414). In embodiments the second device 404 determining the functionality of its components (412) is optional and data related to the functionality of the second device 404 can be sent to the first device 402 without a determination of functionality being processed at the second device 404. The data can be communicated, for example, from the transmitter of the second device 404 to the transceiver of the first device 402.

Still referring to FIG. 4, the data related to the functionality of the components of the second device 404 is received at the first device 402 (416). The first device 402 then retrieves from storage a list that includes at least one predetermined criterion related to the functionality of the components of the second device 404 (418). The predetermined criterion can be, for instance, current, voltage and/or resistance thresholds or ranges used to define the proper operating range. In certain embodiments, for example, the functional check may measure the power supply voltage to determine if it is in an acceptable tolerance. In certain embodiments, the predetermined criterion may be a digital or coded threshold range used to define the proper operating range, whereby, the measured functional test output can be compared to the criterion threshold (e.g., above or below) or compared to the criterion range (e.g., within or outside) to determine functional test status of the component.

Returning to FIG. 4, the first device 402 compares the data related to the functionality of the second device 404 with the list including the at least one predetermined criterion (420) to determine if the second device 404 is functioning properly (422). In certain embodiments, the first device 402 annunciates or otherwise communicates an alarm to alert a user if it is determined that the second device 404 is not functioning properly (424). The alarm may be at least one of an audio alarm, a vibratory alarm, and a visual alarm.

In certain embodiments, the first device 402 does not have to poll the second device 404 to perform the functionality check if the second device 404 automatically performs the functionality check at predetermined intervals and automatically sends a signal or data related to the functionality of the second device 404 to the first device 402. In this manner, in certain embodiments, if the first device 402 does not automatically receive a signal or data related to the functionality of the second device 404 within a predetermined time period, then the first device 402 will annunciate an alarm to alert the user that the second device 404 is not functioning properly.

Figure 5:
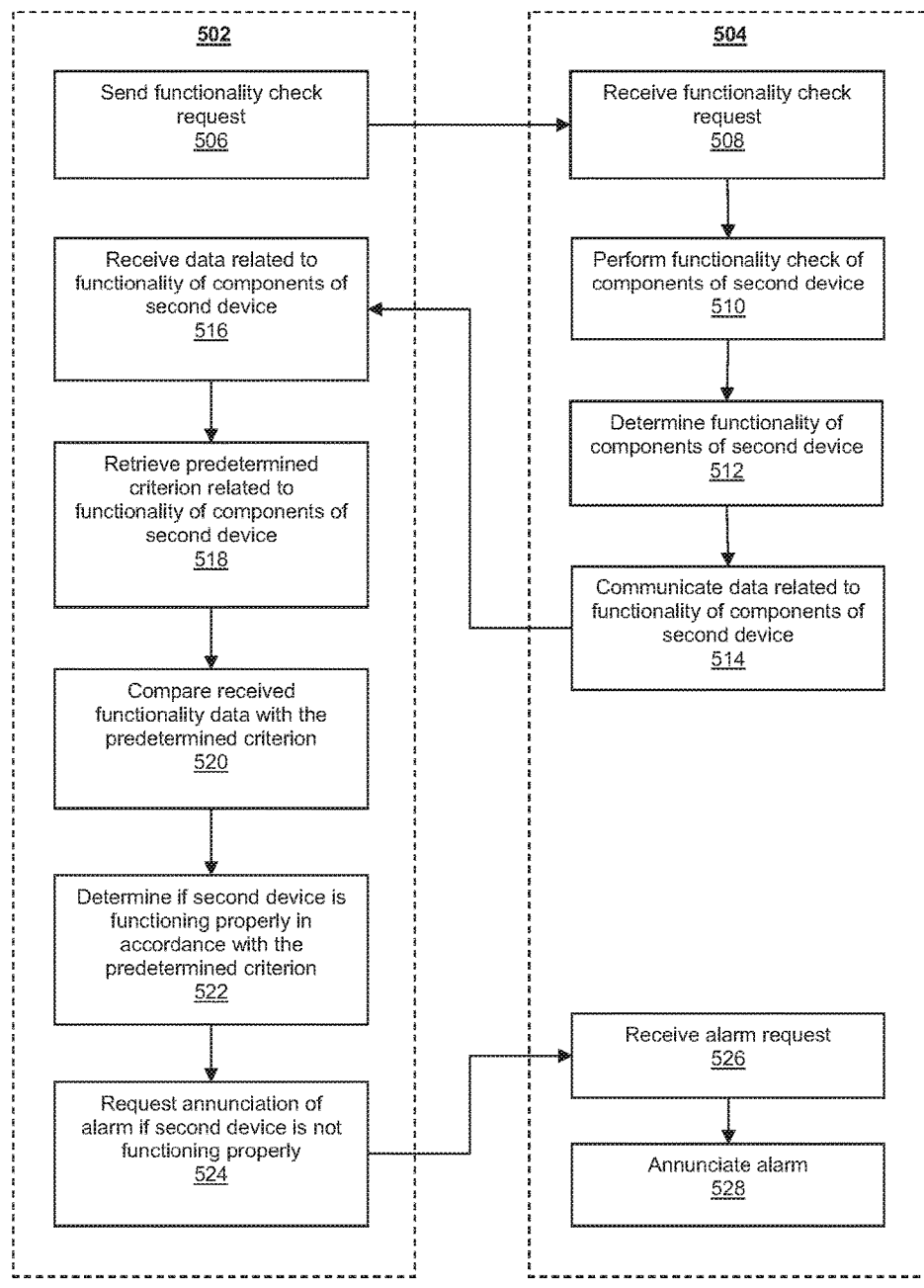
FIG. 5 is a flowchart illustrating a method for mitigating single point failure of at least one device in an analyte monitoring system in accordance with certain embodiments of the present disclosure.

FIG. 5 is a flow diagram illustrating steps in an embodiment for mitigating single point failure of at least one device in an analyte monitoring system 500. The first device 502 and the second device 504 in the analyte monitoring system 500 can be at least one of a receiver device, an analyte meter, a glucose monitor, an insulin pump, a continuous analyte monitor, a cellular phone, a personal digital assistant, a personal computer, a laptop computer, and/or a repeater unit. Execution of the method begins at process block (506) when a first device 502 sends a request that a functionality check of the components of a second device 504 be performed. The request can be sent, for example, wirelessly from the transmitter of the first device 502 to the transceiver of the second device 504. The components of the second device 504 include at least one of a microprocessor, a power supply, a sensor, an electronic component, and a storage device.

Referring to FIG. 5, the second device 504 receives the request to perform a functionality check from the first device 502 (508) and the second device 504 performs the functionality check of its components (510). In certain embodiments, the second device 504 only performs the functionality check if the second device 504 has the capacity to perform the check. The functionality check of the components can include a determination of the current, voltage, and/or resistance that can be measured across an electrical circuit in the components. Additionally, the functionality check can include component testing that applies an input to the various components being tested, and receives an output based on the input. The functionality check may also include checking digital system components, such as a checksum for a block of memory. Any of a number of common techniques used in electronic devices can be applied to this invention. In addition, some components of the devices in the analyte monitoring system may have built in self-test functionality that can be queried, for instance, a power supply module may have a digital self-test status output that can be queried by the processor in order to determine the functionality of the power supply. Also, a device may have electronic circuitry that includes electronic or mechanical switches that allow testing of the electronic circuitry. The switch, for example, could route the current path for functional test across the speaker circuit to test for the proper speaker resistance, in order to detect any open or short circuits.

Referring back to FIG. 5, the second device 504 determines the functionality of its components based on the outcome of the functionality check (512) and communicates data related to the determined functionality of its components to the first device 502 (514). The data can be communicated, for example, from the transmitter of the second device 504 to the transceiver of the first device 502. In certain embodiments, the second device 504 may communicate data related to the functionality of its components to the first device 502 without determining the functionality of the components at the second device 504 itself. The data related to the functionality of the components of the second device 504 is then received at the first device 502 (516) and the first device 502 retrieves from storage a list that includes at least one predetermined criterion related to the functionality of the components of the second device 504 (518). The predetermined criterion can be, for instance, current, voltage and/or resistance thresholds or ranges used to define the proper operating range. In certain embodiments, the functional check may measure the power supply voltage to determine if it is in an acceptable tolerance. In certain embodiments, the predetermined criterion may be a digital or coded threshold range used to define the proper operating range. The measured functional test output can be compared to the criterion threshold (e.g., above or below) or compared to the criterion range (e.g., within or outside) to determine functional test status of the component.

Referring still to FIG. 5, the first device 502 compares the data related to the functionality of the second device 504 with the list including the at least one predetermined criterion at process block (520) and determines if the second device 504 is functioning properly (522). If it is determined that the second device 504 is not functioning properly, the first device 502 requests that the second device 504 annunciate an alarm to alert a user that the second device 504 is not functioning properly (524). The request may be sent from the transmitter of the first device 502 to the transceiver of the second device 504. The second device 504 receives the request from the first device 502 to annunciate the alarm to alert the user of its lack of proper functionality (526) and then annunciates the corresponding alarm (528). The alarm may be at least one of an audio alarm, a vibratory alarm, and a visual alarm.

Figure 6:
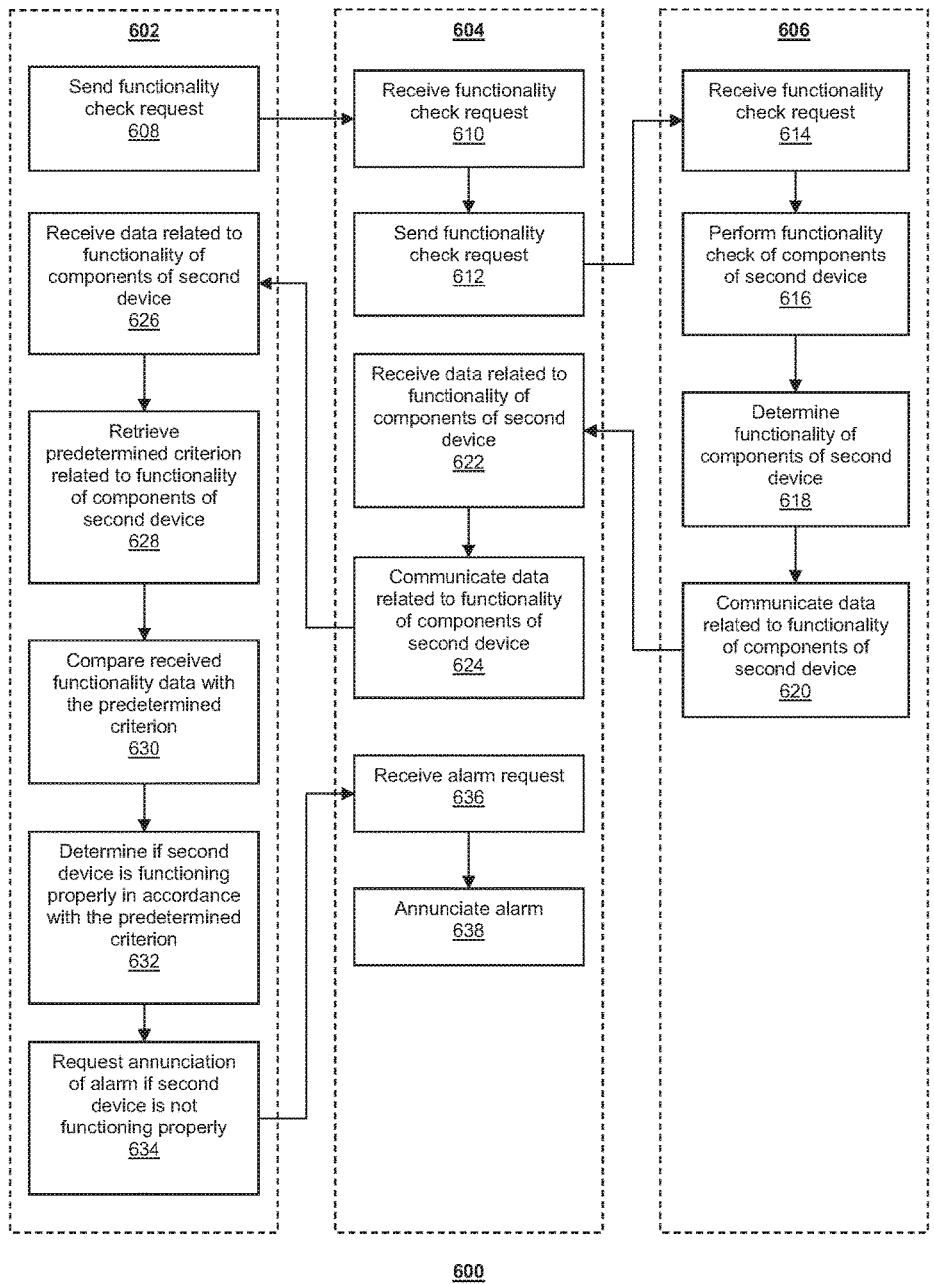
FIG. 6 is a flowchart illustrating a method for mitigating single point failure of at least one device in an analyte monitoring system in accordance with certain embodiments of the present disclosure.

FIG. 6 is a flow diagram illustrating steps in one embodiment for mitigating single point failure of at least one device in an analyte monitoring system 600 that includes a first device 602, a repeater unit 604, and a second device 606. The first device 602 can include at least one of a receiver unit, an analyte meter, a cellular phone, a personal digital assistant, a personal computer, a laptop computer, and an insulin pump. The repeater unit 604 can be operatively or physically coupled to second device 606. The second device can be an analyte sensor and/or a continuous glucose monitor.

Referring to FIG. 6, in certain embodiments, the first device 602 sends a request to the repeater unit 604 that the second device 606 perform a functionality check of its components (608). The request can be sent, for example, wirelessly from the transmitter of the first device 602 to the transceiver of the repeater unit 604. The repeater unit 604 receives the request from the first device 602 (610) and sends, to the second device 606, a request to perform a functionality check of the components of the second device 606 (612). The request may be sent, for example, wirelessly from the transmitter of the repeater unit 604 to the transceiver of the second device 606.

Still referring to FIG. 6, the request to perform a functionality check of its components is received at the second device 606 (614) and, if it is functioning in a high enough capacity, the second device 606 performs the functionality check of one or more of its components (616). In certain embodiments, the functionality check of the components can include a determination of the current, voltage, and/or resistance that can be measured across an electrical circuit in the one or more components. Additionally, the functionality check can include component testing that applies an input to the various components being tested, and receives an output based on the input. The functionality check may also include checking digital system components, such as a checksum for a block of memory. Any of a number of common techniques used in electronic devices can be applied to this invention. In addition, some components of the devices in the analyte monitoring system may have built in self-test functionality that can be queried, for instance, a power supply module may have a digital self-test status output that can be queried by the processor in order to determine the functionality of the power supply. Also, a device may have electronic circuitry that includes electronic or mechanical switches that allow testing of the electronic circuitry. The switch, for example, could route the current path for functional test across the speaker circuit to test for the proper speaker resistance, in order to detect any open or short circuits.

Returning to FIG. 6, the second device 606 determines the functionality check of its components based upon the results of the functionality check (618) and data related to the results of the functionality check are then communicated from the second device 606 to the repeater unit 604 (620). The data can be communicated, for example, wirelessly from the transmitter of the second device 606 to the transceiver of the repeater unit 604. The repeater unit 604 receives the data related to the results of the functionality check of the one or more components of the second device 606 (622) and communicates the data related to the results of the functionality check of the second device 606 to the first device 602 (624). The data can be communicated, for example, wirelessly from the transmitter of the repeater unit 604 to the transceiver of the first device 602. The data related to the functionality check of the one or more components of the second device 606 is then received at the first device 602 (626). The first device 602 retrieves from storage a list including at least one predetermined criterion related to the functionality of the one or more components of the second device (628) and compares the data related to the results of the functionality check with the list including the at least one predetermined criterion (630). The predetermined criterion can be, for instance, current, voltage and/or resistance thresholds or ranges used to define the proper operating range. For instance, the functional check may measure the power supply voltage to determine if it is in an acceptable tolerance. Additionally, the predetermined criterion may be a digital or coded threshold range used to define the proper operating range. The measured functional test output can be compared to the criterion threshold (e.g., above or below) or compared to the criterion range (e.g., within or outside) to determine functional test status of the component. The first device 602 then determines if the second device 604 is functioning in accordance with the at least one predetermined criterion (632) and, if it is determined that the second device 606 is not functioning in accordance with the at least one predetermined criterion, requests that the repeater unit 604 annunciate an alarm (634). The request can be sent, for example, from the transmitter of the first device 602 to the transceiver of the repeater unit 604. The repeater unit 604 receives the request from the first device 602 to annunciate an alarm to alert a user that the second device 606 is not functioning properly (636) and accordingly an alarm is annunciated by the repeater unit 604 (638). The alarm may include at least one of an audio alarm, a vibratory alarm, and a visual alarm that is produced at the repeater unit 604.

In certain embodiments, the first device 602 does not have to send a request to the repeater unit 604 if the repeater unit 604 automatically polls the second device 606 to perform the functionality check or if the second device 606 automatically performs the functionality check at predetermined intervals and then automatically sends this information to the repeater unit 604. In this instance, if the repeater unit 604 does not receive a signal or data related to the functionality of the second device 606, then the repeater unit 604 can annunciate an alarm to alert the user that the second device 606 is not functioning properly.

Figure 7:
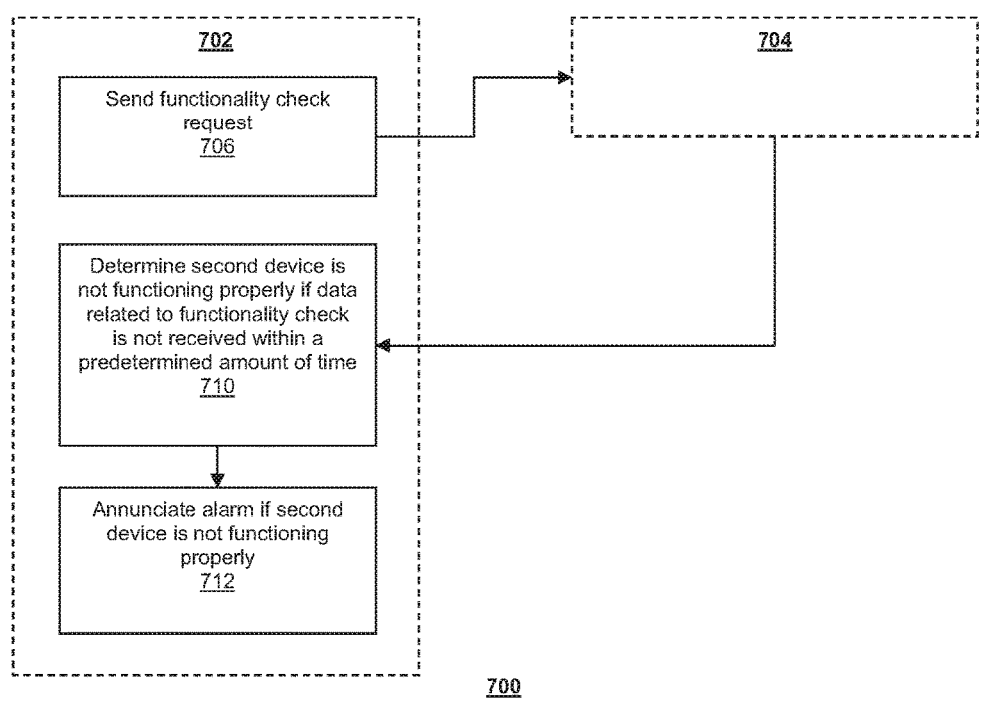
FIG. 7 is a flowchart illustrating a method for mitigating single point failure of at least one device in an analyte monitoring system in accordance with certain embodiments of the present disclosure.

FIG. 7 is a flow diagram illustrating an embodiment for mitigating single point failure of the transmitter of at least one device in an analyte monitoring system 700 that includes a first device 702 and a second device 704. The first device 702 sends a request to a second device 704 to perform a functionality check of the components of the second device 704 (706). If a signal or data has not been received at the first device 702 within a predetermined amount of time, then the first device 702 determines that at least one of the components of the second device 704 is not functioning properly (710) and annunciates an alarm to alert a user that the second device 704 is not functioning properly (712).

In certain embodiments, the first device 702 does not have to request that the second device 704 perform a functionality check of its components, as the second device 704 automatically performs the functionality check at predetermined intervals and then automatically sends data related to the results of the functionality check to the first device 702. In this instance, if the first device 702 does not automatically receive data related to the functionality of the second device 704, then the first device 702 determines that the second device 704 is not functioning properly and annunciates an alarm at the first device 702 to alert the user.

In certain embodiments, the analyte monitoring system includes at least one transmitter attached to the continuous analyte sensor, the receiver device, and the insulin pump. In certain embodiments, the receiver device and/or the insulin pump will detect if the transmitter in the continuous analyte sensor stops functioning. In certain embodiments, the insulin pump and/or the continuous analyte sensor will detect if the transmitter in the receiver device stops functioning. In certain embodiments, the receiver device and/or the continuous analyte sensor will detect if the transmitter in the insulin pump stops functioning.

In certain embodiments, a computer-implemented method for mitigating single point failure of at least one device in an analyte monitoring system includes requesting that a functionality check of one or more components of a first device be performed and that data related to the functionality check of the one or more components of the first device be communicated to a second device, receiving information from the first device that is related to functionality of the one or more components of the first device, communicating the information related to the functionality of the one or more components of the first device to a third device, receiving a request from the third device that an alarm be annunciated if it is determined by the third device that the one or more components of the first device is not functioning in accordance with at least one predetermined criterion, and annunciating an alarm to alert a user that the one or more components of the first device is not functioning in accordance with the at least one predetermined criterion.

In certain aspects, the first device is a continuous glucose monitor.

In certain aspects, the second device includes a repeater unit operatively coupled to the continuous glucose monitor.

In certain aspects, the third device includes one of a receiver device or an insulin pump.

In certain aspects, the one or more components of the first device include at least one of a microprocessor, a power supply, a sensor, and an electronic component.

In certain aspects, the alarm includes at least one of an audio alarm, a vibratory alarm, and a visual alarm.

Certain aspects include receiving a request from the third device that a functionality check of one or more components of a first device be performed and that data related to the functionality check of the one or more components of the first device be communicated to the third device, wherein the request is received at the second device, the second device being operatively coupled to the first device.

In certain aspects, the information related to the functionality of the one or more components of the first device includes a lack of data being received from the first device.

Certain aspects include that the functionality check includes at least one of a determination of a current, a voltage, and a resistance that is measured across an electrical circuit in the one or more components, applying an input to the one or more components and receiving an output from the one or more components, a digital check of the one or more components, a checksum of a memory of the first device, a self-test output check of the one or more components, and an electrical or mechanical test of at least one switch of the one or more components.

Certain embodiments include the at least one predetermined criterion including at least one of a current, a voltage, and a resistance threshold used to define a proper operating range of the first device, a power supply measurement that defines an acceptable tolerance, and a digital threshold range used to define a proper operating range.

In certain embodiments, a computer-implemented method for mitigating single point failure of at least one device in an analyte monitoring system includes requesting that a functionality check of one or more components of a first device be performed and that data related to the functionality check of the one or more components of the first device be communicated to a second device, receiving the data related to the functionality of the one or more components of the first device, retrieving a list including at least one predetermined criterion related to the functionality of the one or more components of the first device from a storage component of the second device, comparing the data related to the functionality of the one or more components of the first device with the list including the at least one predetermined criterion, and determining if the one or more components of the first device is functioning in accordance with the at least one predetermined criterion.

Certain aspects include requesting that an alarm be annunciated at a third device to alert a user if it is determined by the second device that the one or more components of the first device is not functioning in accordance with the at least one predetermined criterion.

In certain aspects, the third device is operatively coupled to the first device.

In certain aspects, the request for the functionality check is received by a third device and the third device polls the first device to perform the functionality check.

Certain aspects include annunciating an alarm operatively coupled to the second device to alert a user if it is determined that the one or more components of the first device is not functioning in accordance with the at least one predetermined criterion.

In certain aspects, the first device is a continuous glucose monitor.

In certain aspects, the second device is one of a receiver device or an insulin pump.

In certain aspects, the third device is a repeater unit operatively coupled to the continuous glucose monitor.

In certain aspects, the one or more first components of the first device include at least one of a microprocessor, a power supply, a sensor, and an electric component.

In certain aspects, the alarm includes at least one of an audio alarm, a vibratory alarm, and a visual alarm.

Certain aspects include that the functionality check includes at least one of a determination of a current, a voltage, and a resistance that is measured across an electrical circuit in the one or more components, applying an input to the one or more components and receiving an output from the one or more components, a digital check of the one or more components, a checksum of a memory of the first device, a self-test output check of the one or more components, and an electrical or mechanical test of at least one switch of the one or more components.

Certain aspects include that the at least one predetermined criterion includes at least one of a current, a voltage, and a resistance threshold used to define a proper operating range of the first device, a power supply measurement that defines an acceptable tolerance, and a digital threshold range used to define a proper operating range.

In certain embodiments, a computer-implemented method for mitigating single point failure of at least one device in an analyte monitoring system includes requesting that a functionality check of one or more components of a first device be performed and that data related to the functionality check of the one or more components of the first device be communicated to a second device, and determining that the one or more components of the first device is not functioning properly if the data related to the functionality check of the components of the first device is not received at the second device, wherein an alarm is annunciated from at least one of the second device or a third device to alert a user that one or more components of the first device is not functioning properly.

Various other modifications and alterations in the structure and method of operation of the embodiments of the present disclosure will be apparent to those skilled in the art without departing from the scope and spirit of the present disclosure. Although the present disclosure has been described in connection with certain embodiments, it should be understood that the present disclosure as claimed should not be unduly limited to such embodiments. It is intended that the following claims define the scope of the present disclosure and that structures and methods within the scope of these claims and their equivalents be covered thereby.

What is claimed is:

1. A computer-implemented method for mitigating single point failure of at least one device in an analyte monitoring system, comprising:
   providing a request, from a first device to a second device, that a functionality check of one or more components of a third device be performed, wherein the functionality check includes communicating, from the third device to the second device, data related to results of the functionality check;
   receiving, at the first device, the data related to the results of the functionality check from the second device;
   determining, by the first device, that the one or more components of the third device is not functioning in accordance with at least one predetermined criterion; and
   providing, to the second device, a request from the first device that an alarm function be initiated to alert a user that the one or more components of the third device is not functioning in accordance with the at least one predetermined criterion.

2. The method of claim 1, wherein the first device comprises one of a receiver device or an insulin pump.

3. The method of claim 1, wherein the second device is a repeater.

4. The method of claim 1, wherein the third device is a continuous glucose monitor.

5. The method of claim 1, wherein the request from the first device to the second device is provided over a RF communication link.

6. The method of claim 1, wherein the data related to the results of the functionality check includes a lack of data being received from the third device.

7. The method of claim 1, wherein the data related to the results of the functionality check include at least one of a determination of a current, a voltage, and a resistance that is measured across an electrical circuit in the one or more components, applying an input to the one or more components and receiving an output from the one or more components, a digital check of the one or more components, a checksum of a memory of the first device, a self-test output check of the one or more components, and an electrical or mechanical test of at least one switch of the one or more components.

8. The method of claim 1, wherein the at least one predetermined criterion includes at least one of a current, a voltage, and a resistance threshold used to define a proper operating range of the first device, a power supply measurement that defines an acceptable tolerance, and a digital threshold range used to define a proper operating range.

9. The method of claim 1, further comprising initiating an alarm of the first device to alert the user that the one or more components of the third device is not functioning in accordance with the at least one predetermined criterion.

10. The method of claim 1, wherein the third device comprises an analyte sensor including a plurality of electrodes, wherein the plurality of electrodes include a working electrode comprising an analyte-responsive enzyme and a mediator, wherein at least one of the analyte-responsive enzyme and the mediator is chemically bonded to a polymer disposed on the working electrode, and wherein at least one of the analyte-responsive enzyme and the mediator is cross-linked with the polymer.

11. An apparatus, comprising:
a communication interface;
one or more processors; and
a memory coupled to the one or more processors, the memory storing instructions which, when executed by the one or more processors, causes the one or more processors to:
provide a request to a second device, using the communication interface, that a functionality check of one or more components of a third device be performed, wherein the functionality check includes communicating, from the third device to the second device, data related to results of the functionality check;
receive, using the communication interface, the data related to the results of the functionality check from the second device;
determine that the one or more components of the third device is not functioning in accordance with at least one predetermined criterion; and
provide, to the second device using the communication interface, a request that an alarm function be initiated to alert a user that the one or more components of the third device is not functioning in accordance with the at least one predetermined criterion.

12. The apparatus of claim 11, further comprising an insulin pump.

13. The apparatus of claim 11, wherein the second device is a repeater.

14. The apparatus of claim 11, wherein the third device is a continuous glucose monitor.

15. The apparatus of claim 11, wherein the communication interface is a RF communication interface.

16. The apparatus of claim 11, wherein the data related to the results of the functionality check includes a lack of data being received from the third device.

17. The apparatus of claim 11, wherein the data related to the results of the functionality check include at least one of a determination of a current, a voltage, and a resistance that is measured across an electrical circuit in the one or more components, applying an input to the one or more components and receiving an output from the one or more components, a digital check of the one or more components, a checksum of the memory of the apparatus, a self-test output check of the one or more components, and an electrical or mechanical test of at least one switch of the one or more components.

18. The apparatus of claim 11, wherein the at least one predetermined criterion includes at least one of a current, a voltage, and a resistance threshold used to define a proper operating range of the apparatus, a power supply measurement that defines an acceptable tolerance, and a digital threshold range used to define a proper operating range.

19. The apparatus of claim 11, further comprising an alarm coupled to the one or more processors, and wherein the memory storing instructions which, when executed by the one or more processors, causes the one or more processors to initiate the alarm coupled to the one or more processors to alert the user that the one or more components of the third device is not functioning in accordance with the at least one predetermined criterion.

20. The apparatus of claim 11, wherein the third device comprises an analyte sensor including a plurality of electrodes, wherein the plurality of electrodes include a working electrode comprising an analyte-responsive enzyme and a mediator, wherein at least one of the analyte-responsive enzyme and the mediator is chemically bonded to a polymer disposed on the working electrode, and wherein at least one of the analyte-responsive enzyme and the mediator is cross-linked with the polymer.

* * * * *